United States Patent
Awadh et al.

(10) Patent No.: US 11,124,465 B2
(45) Date of Patent: Sep. 21, 2021

(54) HYDRODESULFURIZATION CATALYST WITH A ZEOLITE-GRAPHENE MATERIAL COMPOSITE SUPPORT AND METHODS THEREOF

(71) Applicant: King Fahd University of Petroleum and Minerals, Dhahran (SA)

(72) Inventors: Tawfik Abdo Saleh Awadh, Dhahran (SA); Islam Ali Elsayed, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/521,229

(22) Filed: Jul. 24, 2019

(65) Prior Publication Data
US 2021/0024436 A1 Jan. 28, 2021

(51) Int. Cl.
*C07C 1/32* (2006.01)
*B01J 21/18* (2006.01)
(Continued)

(52) U.S. Cl.
CPC ............... *C07C 1/322* (2013.01); *B01J 21/18* (2013.01); *B01J 29/166* (2013.01);
(Continued)

(58) Field of Classification Search
CPC ..... C07C 1/322; C07C 7/163; C07C 2521/18; C07C 2529/08; C07C 2602/28;
(Continued)

(56) References Cited

U.S. PATENT DOCUMENTS

| | | | |
|---|---|---|---|
| 4,318,801 A | 3/1982 | Lese et al. | |
| 9,631,148 B2 | 4/2017 | Worsley et al. | |
| 2014/0275684 A1* | 9/2014 | Bielawski | B01J 21/185 585/653 |

FOREIGN PATENT DOCUMENTS

| | | |
|---|---|---|
| CN | 106238075 A | 12/2016 |
| CN | 107362825 A | 11/2017 |

(Continued)

OTHER PUBLICATIONS

Xu, et al. ; Hexamethonium bromide-assisted synthesis of CoMo/graphene catalysts for selective hydrodesulfurization ; Applied Catalysis B: Environmental, vol. 244 ; pp. 385-395 ; May 5, 2019 ; Abstract Only ; 2 Pages.

(Continued)

*Primary Examiner* — Brian A McCaig
(74) *Attorney, Agent, or Firm* — Oblon, McClelland, Maier & Neustadt, L.L.P.

(57) ABSTRACT

A hydrodesulfurization catalyst, which includes (i) a catalyst support including a zeolite doped with 0.1 to 0.5 wt. % of a graphene material, based on a total weight of the catalyst support, (ii) 5 to 20 wt. % of molybdenum, based on a total weight of the hydrodesulfurization catalyst, and (iii) 1 to 6 wt. % of a promoter selected from the group consisting of cobalt and nickel, based on a total weight of the hydrodesulfurization catalyst. The molybdenum and the promoter are homogeneously disposed on the catalyst support. A method of producing the hydrodesulfurization catalyst via incipient wetness impregnation techniques, and a method for desulfurizing a hydrocarbon feedstock with the hydrodesulfurization catalyst are also provided.

20 Claims, 30 Drawing Sheets

(51) Int. Cl.
  *B01J 29/16* (2006.01)
  *B01J 35/10* (2006.01)
  *B01J 37/02* (2006.01)
  *B01J 37/00* (2006.01)
  *B01J 37/08* (2006.01)
  *C10G 49/04* (2006.01)

(52) U.S. Cl.
  CPC ....... *B01J 35/1019* (2013.01); *B01J 35/1038* (2013.01); *B01J 35/1061* (2013.01); *B01J 37/009* (2013.01); *B01J 37/0201* (2013.01); *B01J 37/0236* (2013.01); *B01J 37/08* (2013.01); *C10G 49/04* (2013.01); *C07C 2521/18* (2013.01); *C07C 2529/08* (2013.01)

(58) Field of Classification Search
  CPC ........ C10G 45/12; C10G 49/04; B01J 29/166; B01J 29/18; B01J 35/1019; B01J 35/1038; B01J 35/1061; B01J 37/009; B01J 37/0201; B01J 37/0236; B01J 37/08
  See application file for complete search history.

(56) References Cited

FOREIGN PATENT DOCUMENTS

| | | |
|---|---|---|
| EP | 2 985 079 B1 | 10/2018 |
| WO | 2017/185928 A1 | 11/2017 |

OTHER PUBLICATIONS

Hajjar, et al. ; Optimizing parameters affecting synthesis of a novel Co—Mo/Go catalyst in a Naphtha HDS reaction utilizing D-optimal experimental design method ; Journal of the Taiwan Institute of Chemical Engineers, vol. 78 ; pp. 566-575 ; Sep. 2017 ; Abstract Only ; 2 Pages.

Hajjar, et al. ; Graphene based catalysts for deep hydrodesulfurization of naphtha and diesel fuels: A physiochemical study; Fuel, vol. 165 ; pp. 468-476 ; Feb. 1, 2016 ; Abstract Only ; 2 Pages.

* cited by examiner

Si Kα1

C Kα1_2

O Kα1

Al Kα1

Mo La1

Ni Ka1

HYDRODESULFURIZATION CATALYST WITH A ZEOLITE-GRAPHENE MATERIAL COMPOSITE SUPPORT AND METHODS THEREOF

STATEMENT OF ACKNOWLEDGEMENT

The inventors acknowledge King Fand University of Petroleum and Minerals (KFUPM) and the chemistry department at KFUPM for support.

BACKGROUND OF THE INVENTION

Field of the Invention

The present invention relates to a hydrodesulfurization catalyst that contains a zeolite doped with a graphene material as a catalyst support and methods of making and using the hydrodesulfurization catalyst for desulfurizing hydrocarbon feedstocks.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Air pollution caused by sulfur dioxide emissions is an environmental concern that has prompted the use of fuel with ultra-low sulfur content. To meet the strict environmental regulations for sulfur content in petroleum products, deep desulfurization has become necessary. See D. Xu, W. Zhu, H. Li, J. Zhang, F. Zou, H. Shi, Y. Yan, Oxidative desulfurization of fuels catalyzed by $V_2O_5$ in ionic liquids at room temperature, Energy and Fuels. 23 (2009) 5929-5933; S. Nassreddine, S. Casu, J. L. Zotin, C. Geantet, L. Piccolo, Thiotolerant $Ir/SiO_2-Al_2O_3$ bifunctional catalysts: Effect of support acidity on tetralin hydroconversion, Catal. Sci. Technol. 1 (2011) 408-412; M. Breysse, G. Djega-Mariadassou, S. Pessayre, C. Geantet, M. Vrinat, G. Pérot, M. Lemaire, Deep desulfurization: Reactions, catalysts and technological challenges, Catal. Today. 84 (2003) 129-138; and T. C. Ho, J. M. McConnachie, Ultra-deep hydrodesulfurization on $MoS_2$ and $Co_{0.1}MoS_2$: Intrinsic vs. environmental factors, J. Catal., 277 (2011) 117-122, each incorporated herein by reference in their entirety. The use of catalytic hydrotreating for the reduction of sulfur content in diesel fuel has become a very intensive research area recently. Environmental regulations dictate that the sulfur content in diesel and gasoline should be lowered to 10 to 50 ppm. See C. Song, X. Ma, New design approaches to ultra-clean diesel fuels by deep desulfurization and deep dearomatization, Appl. Catal. B Environ. 41 (2003) 207-238; and A. Duan, G. Wan, Z. Zhao, C. Xu, Y. Zheng, Y. Zhang, T. Dou, X. Bao, K. Chung, Characterization and activity of Mo supported catalysts for diesel deep hydrodesulphurization, Catal. Today, 119 (2007) 13-18, each incorporated herein by reference in their entirety. In refinery processes, hydrodesulfurization (HDS) has been used extensively to reduce sulfur containing compounds in various petroleum products and intermediates. Hydrodesulfurization catalysts have attracted researchers due to their excellent properties such as activity, product longevity and selectivity. Refractory sulfur such as 4,6-dimethyl dibenzothiophene (4,6-DMDBT) and dibenzothiophene (DBT) are the most difficult to remove, and pose significant challenges in meeting the ultra-low sulfur content environmental requirements. See U.T. Turaga, C. Song, MCM-41-supported Co-Mo catalysts for deep hydrodesulfurization of light cycle oil, Catal. Today. 86 (2003) 129-140; C. Song, X. Ma, New design approaches to ultra-clean diesel fuels by deep desulfurization and deep dearomatization, Appl. Catal. B Environ. 41 (2003) 207-238; I. Fechete, Y. Wang, J. C. Védrine, The past, present and future of heterogeneous catalysis, Catal. Today. 189 (2012) 2-27; and Y. Fan, H. Xiao, G. Shi, H. Liu, Y. Qian, T. Wang, G. Gong, X. Bao, Citric acid-assisted hydrothermal method for preparing $NiW/USY-Al_2O_3$ ultradeep hydrodesulfurization catalysts, J. Catal. 279 (2011) 27-35, each incorporated herein by reference in their entirety.

The catalyst support is one factor which can contribute to the catalytic performance of a catalyst. See F. Trejo, M. S. Rana, J. Ancheyta, A. Rueda, Hydrotreating catalysts on different supports and its acid-base properties, Fuel. 100 (2012) 163-172, incorporated herein by reference in its entirety. Zeolites contain both alumina and silica, and have been found to possess desirable surface areas for the dispersion of metals and a high concentration of Lewis and Bronsted acid sites compared to alumina alone, and have thus been used as a support for CoMo and NiMo. See J. C. Amezcua, L. Lizama, C. Salcedo, I. Puente, J. M. Domínguez, T. Klimova, NiMo catalysts supported on titania-modified SBA-16 for 4,6-dimethyldibenzothiophene hydrodesulfurization, Catal. Today. 107-108 (2005) 578-588, incorporated herein by reference in its entirety. Zeolites possess hydrogenating and strong acid sites for accelerating C-S bond cleavage in a variety of different ways. However, the microporous nature of zeolites limits their ability to remove bulky molecules in hydrotreating processes. Therefore, there is a need for synthesizing material with Bronsted acid sites and a high surface area which can accommodate bulky sulfur compounds. See G. Pérot, Hydrotreating catalysts containing zeolites and related materials—Mechanistic aspects related to deep desulfurization, Catal. Today. 86 (2003) 111-128, incorporated herein by reference in its entirety.

Zeolites having a hierarchical structure of micro- and meso-pores and acid-base properties that can be changed during synthesis methods have been used in HDS processes. See T. F. Degnan, Jr., Applications of zeolites in petroleum refining, Top. Catal. 13 (2000) 349-356, incorporated herein by reference in its entirety. Zeolites have also been used as adsorbents due to their capacity for ionic exchange. See V. Akhmedov, S. Al-Khowaiter, Recent advances and future aspects in the selective isomerization of high n-alkanes, Catal. Rev.-Sci. Eng. 49 (2007) 33-139, incorporated herein by reference in its entirety. Zeolites can provide acidity to the catalyst structure while also finely dispersing metal nanoparticles, and thus have been used in a wide variety of applications such as hydrogenation-dehydrogenation and production of high octane gasoline throughout hydroisomerization of $C_5$-$C_6$ n-paraffins. See Q. Zhang, W. Deng, Y. Wang, Recent advances in understanding the key catalyst factors for Fischer-Tropsch synthesis, J. Energy Chem. 22 (2013) 27-38; and E. Heracleous, E. F. Iliopoulou, A. A. Lappas, Microporous/mesoporous Pt/ZSM-5 catalysts for hydroisomerization of BTL-naphtha, Ind. Eng. Chem. Res. 52 (2013) 14567-14573, each incorporated herein by reference in their entirety. Also, these types of catalysts can be used in hydrocracking processes. See P. S. F. Mendes, G. Lapisardi, C. Bouchy, M. Rivallan, J. M. Silva, M. F. Ribeiro, Hydrogenating activity of Pt/zeolite catalysts focusing acid support and metal dispersion influence, Appl. Catal. A Gen. 504 (2015) 17-28, incorporated herein by reference in its entirety. Zeolite beta (BEA) and Y zeolite-based catalysts have been studied due to their surface properties for catalyst dispersion. See H. Deldari, Suitable catalysts for hydroisomerization of long-chain normal paraffins, Appl. Catal. A Gen. 293 (2005) 1-10; K. C. Park, S. K. Ihm, Comparison of Pt/zeolite catalysts for n-hexadecane hydroisomerization, Appl. Catal. A Gen. 203 (2000) 201-209; A. Gutiérrez, J. M. Arandes, P. Castaño, M. Olazar, J. Bilbao, Preliminary studies on fuel production through LCO hydrocracking on noble-metal supported catalysts, Fuel. 94 (2012) 504-515; and W. Zhang, P. G. Smirniotis, Effect of zeolite structure and acidity on the product selectivity and reaction mechanism for n-octane hydroisomerization and hydrocracking, J. Catal. 182 (1999) 400-416, each incorporated herein by reference in their entirety.

Supports such as titania and alumina modified with organic molecules such as monocarboxylic acids, citric acid and phosphonic acid have been reported for the synthesis of supported active metal catalyst. See M. J. Wei, J. Zhou, X. Lu, Y. Zhu, W. Liu, L. Lu, L. Zhang, Diffusion of water molecules confined in slits of rutile TiO2(110) and graphite (0001), Fluid Phase Equilib. 302 (2011) 316-320; and H. Li, M. Li, Y. Chu, F. Liu, H. Nie, Essential role of citric acid in preparation of efficient NiW/Al$_2$O$_3$ HDS catalysts, Appl. Catal. A Gen. 403 (2011) 75-82; L. Li, Y. Wang, K. Shi, S. Chen, Z. Yang, X. Lu, Preparation and characterization of mesoporous MoO$_3$/TiO$_2$ composite with high surface area by self-supporting and ammonia method, Catal. Letters. 142 (2012) 480-485, each incorporated herein by reference in its entirety. For example, the intrinsic role of citric acid includes partly changing into carbonaceous deposits during sulfidation, which may isolate and decrease the WS$_2$ slab length. It may also react with basic and neutral OH groups to moderate the interaction between the active phase and the alumina support. C—NiW/C—Al$_2$O$_3$ was reported to effectively benefit from both roles of citric acid to facilitate the formation of more Ni—W—S active phases. See H. Li, M. Li, Y. Chu, F. Liu, H. Nie, Essential role of citric acid in preparation of efficient NiW/Al$_2$O$_3$ HDS catalysts, Appl. Catal. A Gen. 403 (2011) 75-82, incorporated herein by reference in its entirety.

Graphene is a two-dimensional single sheet of carbon atoms distributed in a hexagonal network. It has a plate like structure that is one atomic layer thick. See M.D. Stoller, S. Park, Y. Zhu, J. An, R. S. Ruoff, Graphene-Based Ultracapacitors, Nano Lett. 8 (2008) 3498-3502, incorporated herein by reference in its entirety. Due to the high surface area, advantageous mechanical properties, and the interesting mechanical, thermal and electronic features of graphene, it has been used in different applications like batteries, solar cells, composite materials as well as catalysts. See P. V. Kamat, Graphene-based nanoassemblies for energy conversion, J. Phys. Chem. Lett. 2 (2011) 242-251; B. F. MacHado, P. Serp, Graphene-based materials for catalysis, Catal. Sci. Technol. 2 (2012) 54-75; and Q. Zhou, Z. Zhao, Y. Zhang, B. Meng, A. Zhou, J. Qiu, Graphene sheets from graphitized anthracite coal: Preparation, decoration, and application, Energy and Fuels. 26 (2012) 5186-5192, each incorporated herein by reference in their entirety. The presence of oxygen in certain graphitic materials can also play a role in enhancing the precursor ions adsorption as it supplies numerous sites of nucleation for the incorporated nanoparticles. See L. Zhu, S. Zhang, Y. Cui, H. Song, X. Chen, One step synthesis and capacitive performance of graphene nanosheets/Mn$_3$O$_4$ composite, Electrochim. Acta. 89 (2013) 18-23, incorporated herein by reference in its entirety.

Catalyst structure, surface atomic arrangement and coordination are very sensitive parameters involved in catalytic reactions, and these parameters can be controlled by tuning the morphology, composition and catalyst size. See Q.-H. Xia, H.-Q. Ge, C.-P. Ye, Z.-M. Liu, K.-X. Su, Advances in Homogeneous and Heterogeneous Catalytic Asymmetric Epoxidation, Chem. Rev. 105 (2005) 1603-1662; J. A. Melero, L. F. Bautista, G. Morales, J. Iglesias, D. Briones, Biodiesel production with heterogeneous sulfonic acid-functionalized mesostructured catalysts, Energy and Fuels. 23 (2009) 539-547; J. Blanco-Galvez, P. Fernández-Ibáñez, S. Malato-Rodríguez, Solar Photocatalytic Detoxification and Disinfection of Water: Recent Overview, J. Sol. Energy Eng. 129 (2007) 4-15; and A. Hu, H.L. Ngo, W. Lin, Chiral porous hybrid solids for practical heterogeneous asymmetric hydrogenation of aromatic ketones, J. Am. Chem. Soc. 125 (2003) 11490-11491, each incorporated herein by reference in their entirety. Different materials have been used as an alternative support for HDS reaction such as MgO, SiO$_2$, ZrO, Al$_2$O$_3$, and mixed oxides. See M. Jia, P. Afanasiev, M. Vrinat, The influence of preparation method on the properties of NiMo sulfide catalysts supported on ZrO$_2$, Appl. Catal. A Gen. 278 (2005) 213-221; H. Shimada, T. Sato, Y. Yoshimura, J. Hiraishi, A. Nishijima, Support effect on the catalytic activity and properties of sulfided molybdenum catalysts, J. Catal. 110 (1988) 275-284; O. Y. Gutiérrez, G. A. Fuentes, C. Salcedo, T. Klimova, SBA-15 supports modified by Ti and Zr grafting for NiMo hydrodesulfurization catalysts, Catal. Today. 116 (2006) 485-497; D. Laurenti, B. Phung-Ngoc, C. Roukoss, E. Devers, K. Marchand, L. Massin, L. Lemaitre, C. Legens, A. A. Quoineaud, M. Vrinat, Intrinsic potential of alumina-supported CoMo catalysts in HDS: Comparison between γc, γt, and δ-alumina, J. Catal. 297 (2013) 165-175; and R. Mbarki, A. Mnif, A.H. Hamzaoui, Structural, dielectric relaxation and electrical conductivity behavior in MgO powders synthesized by sol-gel, Mater. Sci. Semicond. Process. 29 (2015) 300-306, each incorporated herein by reference in their entirety. The role of supports to disperse the active phases on its surface is still not well investigated. See L. Kaluža, D. Gulková, Z. Vít, M. Zdražil, High-activity MgO-supported CoMo hydrodesulfurization catalysts prepared by non-aqueous impregnation, Appl. Catal. B Environ. 162 (2015) 430-436, incorporated herein by reference in its entirety. Despite interest in the development of new supports for catalysts, there is still much work that needs to be done in this area to provide improved catalyst activity and stability.

In view of the forgoing, there is a need for catalysts and catalyst supports that are easy to manufacture, and that provide hydrodesulfurization catalysts with high thermal stability and high desulfurization activity.

SUMMARY OF THE INVENTION

Accordingly, it is one object of the present invention to provide a hydrodesulfurization catalyst that includes a zeolite doped with a graphene material as a catalyst support.

It is another object of the present disclosure to provide methods for producing the hydrodesulfurization catalyst.

It is another object of the present disclosure to provide methods for desulfurizing a hydrocarbon feedstock that contains a sulfur-containing compound(s) using the hydrodesulfurization catalyst.

Thus the present disclosure provides:

A hydrodesulfurization catalyst that contains (i) a catalyst support that includes a zeolite doped with 0.1 to 0.5 wt. % of a graphene material, based on a total weight of the catalyst support, (ii) 5 to 20 wt. % of molybdenum, based on a total weight of the hydrodesulfurization catalyst, and (iii) 1 to 6 wt. % of a promoter selected from the group consisting of cobalt and nickel, based on a total weight of the hydrodesulfurization catalyst, wherein the molybdenum and the promoter are homogeneously disposed on the catalyst support.

In some embodiments, the zeolite is a Y-zeolite.

In some embodiments, the graphene material is present in the catalyst support in an amount of 0.3 to 0.4 wt. %, based on a total weight of the catalyst support.

In some embodiments, the graphene material is graphene oxide.

In some embodiments, molybdenum is present in an amount of 14 to 16 wt. %, and the promoter is present in an amount of 4 to 6 wt. %, each based on a total weight of the hydrodesulfurization catalyst.

In some embodiments, the catalyst support consists of the zeolite doped with the graphene material, and wherein the hydrodesulfurization catalyst consists of the catalyst support, the molybdenum, and the promoter.

In some embodiments, the hydrodesulfurization catalyst has a BET surface area of 290 to 350 m$^2$/g.

In some embodiments, the hydrodesulfurization catalyst has an average pore diameter of 3 to 3.8 nm.

In some embodiments, the hydrodesulfurization catalyst has a total pore volume of 0.25 to 0.30 m$^3$/g.

In some embodiments, the hydrodesulfurization catalyst has a hierarchy factor (HF), defined as a ratio of microporous volume to total pore volume ($V_{micro}/V_{total}$) multiplied by a ratio of mesoporous surface area to BET surface area ($S_{meso}/S_{BET}$) of 0.020 to 0.035.

A method of producing the hydrodesulfurization catalyst that includes impregnating the catalyst support by adding an aqueous solution comprising a molybdenum salt and either a cobalt salt or a nickel salt to a suspension of the catalyst support in water to form a catalyst mixture, filtering the catalyst mixture to obtain a wet catalyst, and drying and calcining the wet catalyst thereby producing the hydrodesulfurization catalyst.

In some embodiments, the catalyst support is formed by mixing together the zeolite, the graphene material, water, an alcohol solvent, and a polymeric dispersant to form a support mixture, and filtering the support mixture to obtain a filtrate and drying the filtrate to form the catalyst support.

A method for desulfurizing a hydrocarbon feedstock that contains a sulfur-containing compound, the method includes contacting the hydrocarbon feedstock with the hydrodesulfurization catalyst in the presence of H$_2$ gas to convert at least a portion of the sulfur-containing compound into a mixture of H$_2$S and a desulfurized product, and removing the H$_2$S from the mixture thereby forming a desulfurized hydrocarbon stream.

In some embodiments, the hydrocarbon feedstock is contacted with the hydrodesulfurization catalyst at a temperature of 150 to 500° C. for 0.1-10 hours.

In some embodiments, a pressure of the H$_2$ gas is from 30 to 80 bars.

In some embodiments, the sulfur-containing compound is present in the hydrocarbon feedstock at a concentration of 100 to 7,000 ppm.

In some embodiments, the sulfur-containing compound is at least one selected from the group consisting of a sulfide, a disulfide, a thiophene, a benzothiophene, and a dibenzothiophene. In some embodiments, the sulfur-containing compound is dibenzothiophene.

In some embodiments, a sulfur content of the desulfurized hydrocarbon stream is less than 10 ppm.

In some embodiments, the hydrocarbon feedstock is contacted with the hydrodesulfurization catalyst by passing the hydrocarbon feedstock through a fixed-bed reactor containing the hydrodesulfurization catalyst.

BRIEF DESCRIPTION OF THE DRAWINGS

The foregoing paragraphs have been provided by way of general introduction, and are not intended to limit the scope of the following claims. A more complete appreciation of the invention and many of the attendant advantages thereof will be readily obtained as the same becomes better understood by reference to the following detailed description when considered in connection with the accompanying drawings, wherein:

DETAILED DESCRIPTION OF THE INVENTION

Figure 1A:
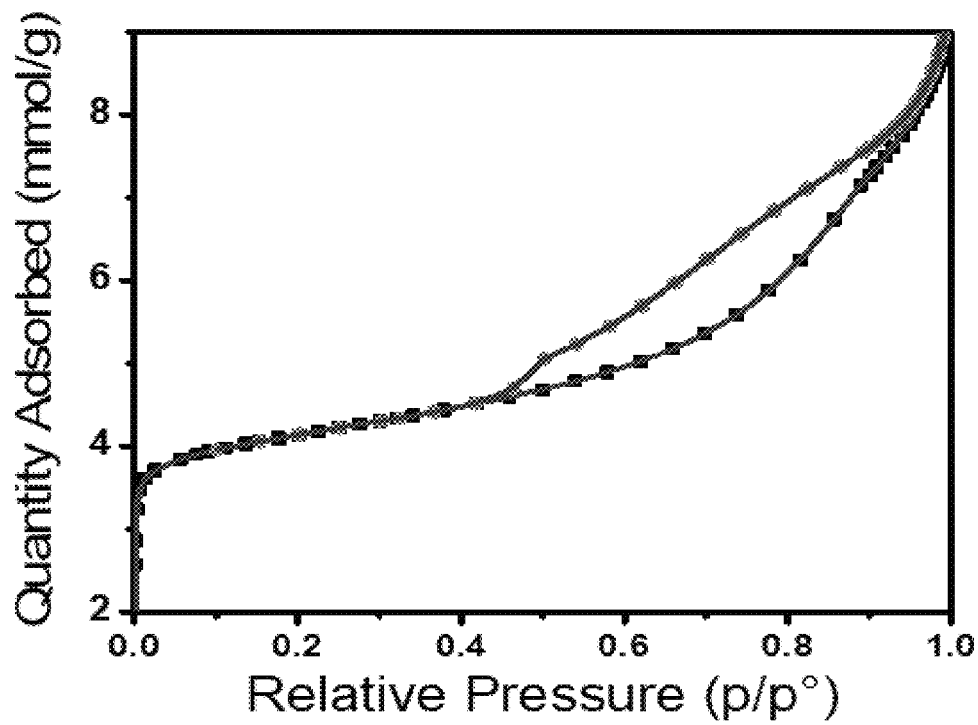
FIGS. 1A-1B illustrate N$_2$ adsorption-desorption (1A) and pore size distribution (1B) for ZMI.
Figure 1B:
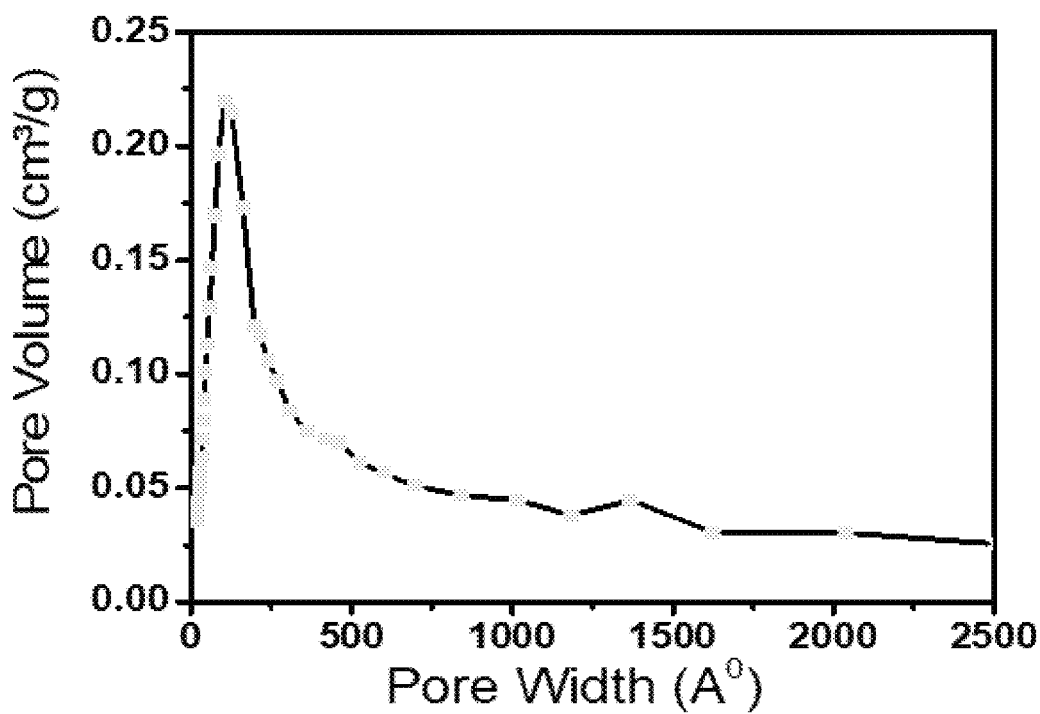
Figure 1C:
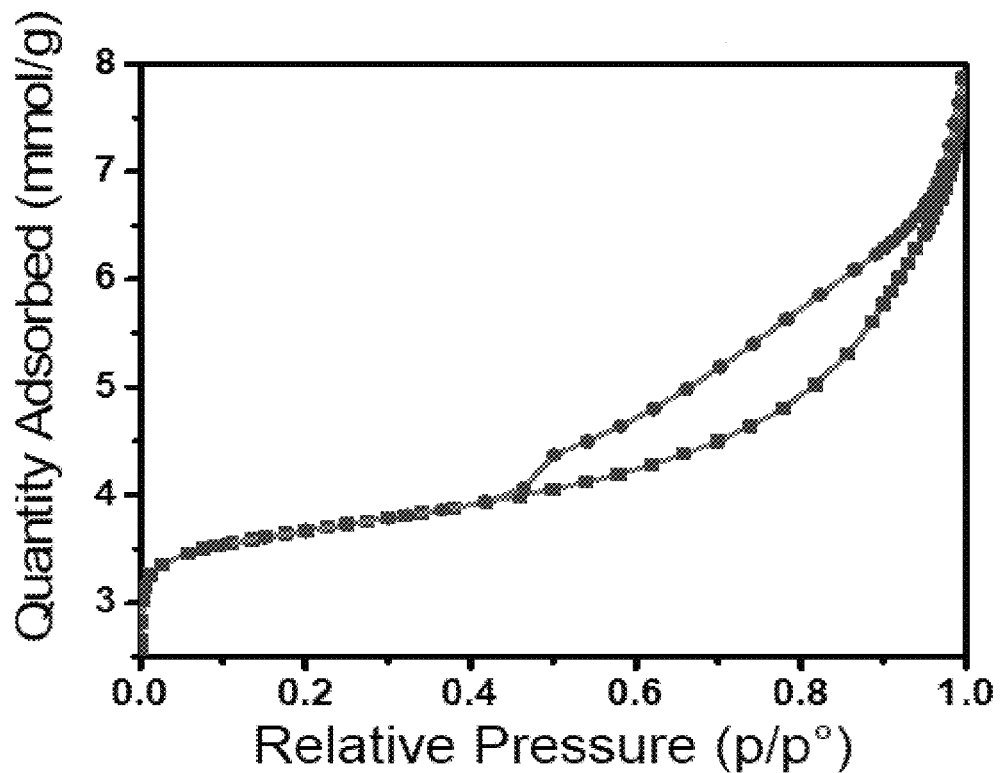
FIGS. 1C-1D illustrate N$_2$ adsorption-desorption (1C) and pore size distribution (1D) for ZMC.
Figure 1D:
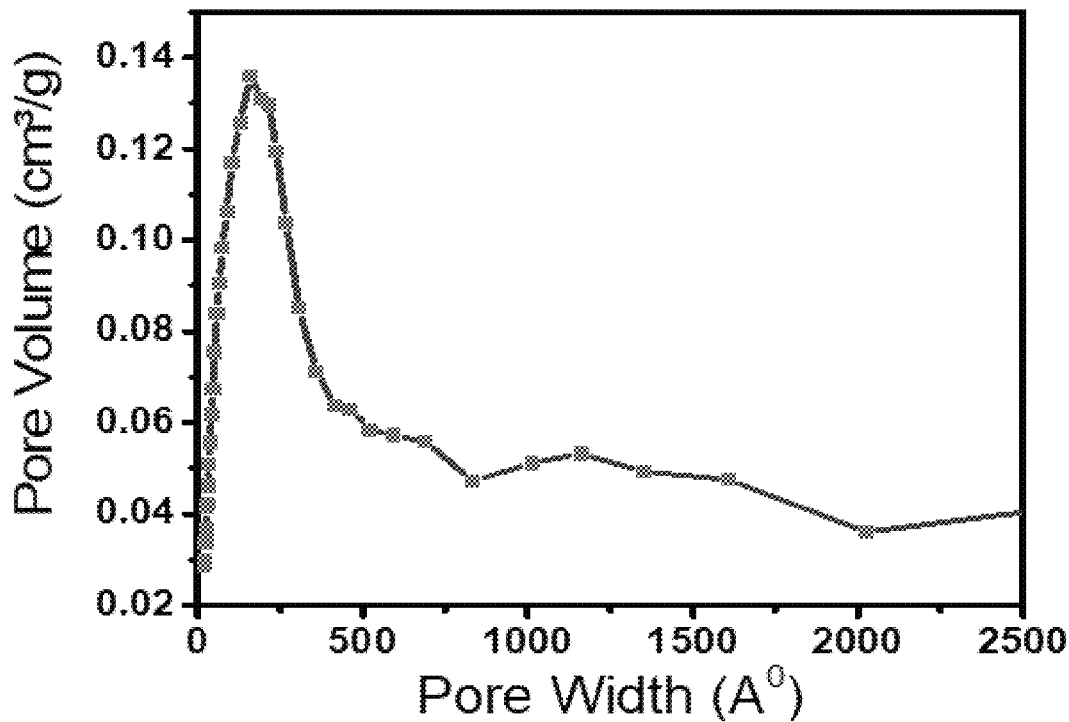
Figure 1E:
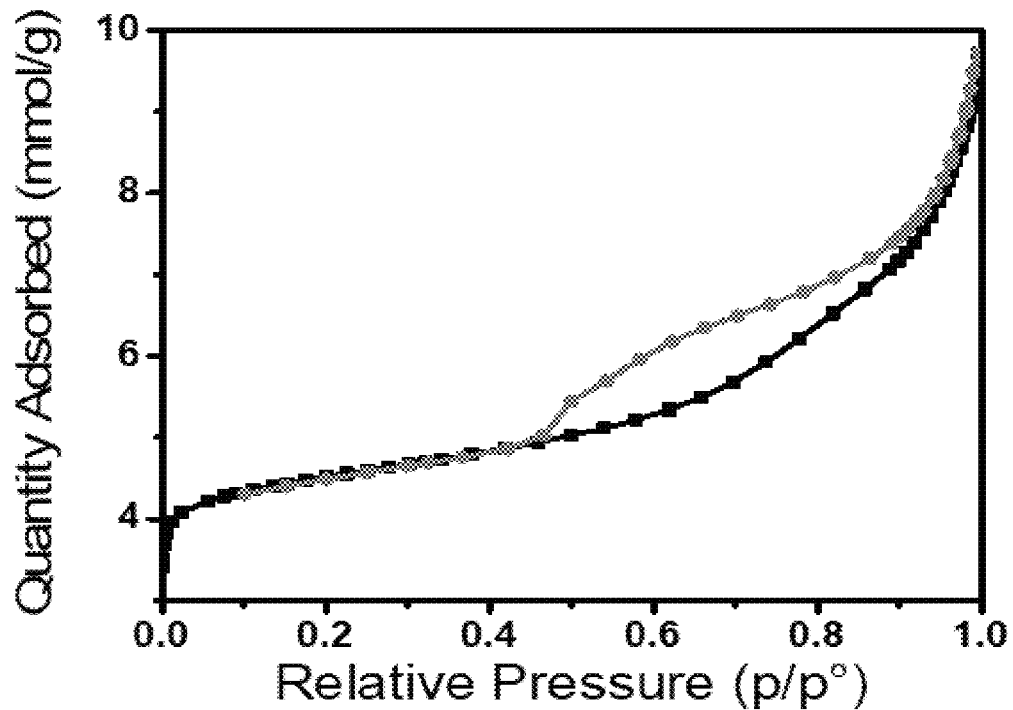
FIGS. 1E-1F illustrate N$_2$ adsorption-desorption (1E) and pore size distribution (1F) for ZGMI.
Figure 1F:
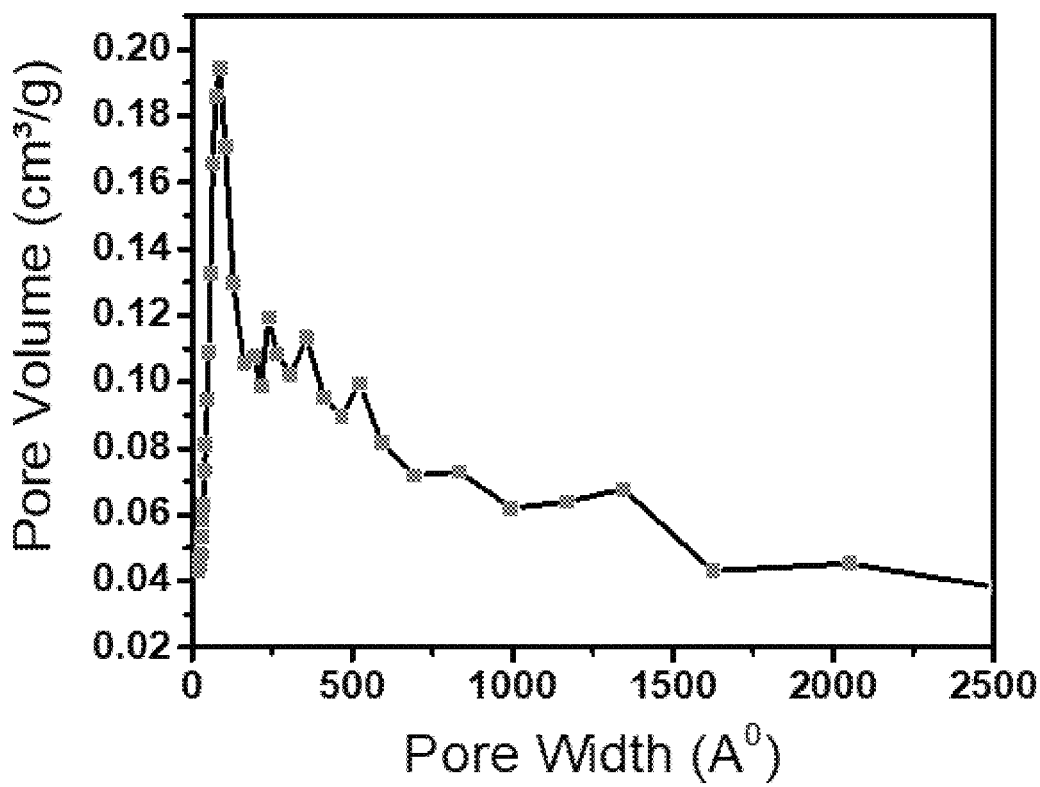
Figure 1G:
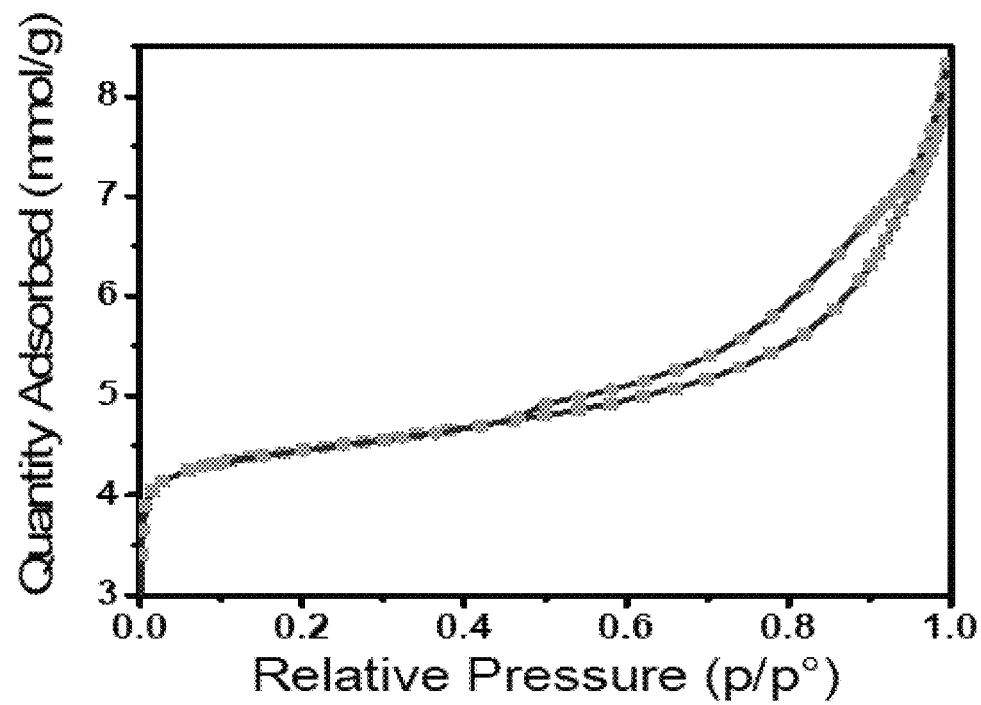
FIGS. 1G-1H illustrate N$_2$ adsorption-desorption (1G) and pore size distribution (1H) for ZGMC.
Figure 1H:
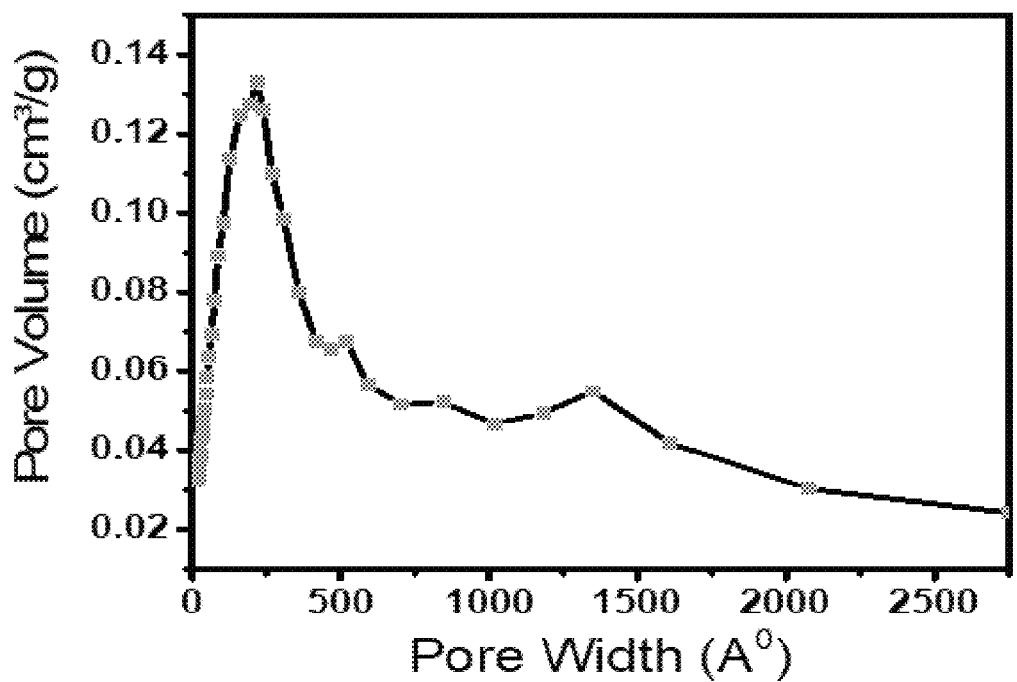

In the following description, it is understood that other embodiments may be utilized and structural and operational changes may be made without departure from the scope of the present embodiments disclosed herein.

Definitions

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

As used herein, the terms "optional" or "optionally" means that the subsequently described event(s) can or cannot occur or the subsequently described component(s) may or may not be present (e.g., 0 wt. %).

The term "alkyl", as used herein, unless otherwise specified, refers to a straight, branched, or cyclic, aliphatic fragment having 1 to 26 carbon atoms, preferably 2 to 24, preferably 3 to 22, preferably 4 to 20, preferably 5 to 18, preferably 6 to 16, preferably 7 to 14, preferably 8 to 12, preferably 9 to 10. Non-limiting examples include, but are not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, lauryl, myristyl, cetyl, stearyl, and the like, including guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), and cycloalkyl groups such as cyclopropyl, cyclobutyl, cyclopentyl, cyclohexyl, norbornyl, and adamantyl.

The present disclosure includes all hydration states of a given salt or formula, unless otherwise noted. For example, nickel(II) acetate includes anhydrous $Ni(OCOCH_3)_2$, and hydrated forms such as the tetrahydrate $(Ni(OCOCH_3)_2 \cdot 4H_2O)$ or any other hydrated forms or mixtures. In another example, ammonium heptamolybdate(VI) includes anhydrous $(NH_4)_6Mo_7O_{24}$, and hydrated forms such as ammonium heptamolybdate tetrahydrate $(NH_4)_6Mo_7O_{24} \cdot 4H_2O$.

As used herein, the term "diameter" (e.g., particle size) of a particle refers to the linear distance measured from one point on the particle through the center of the particle to a point directly across from it. For a circle, an oval, an ellipse, and a multilobe, the term "diameter" refers to the greatest possible distance measured from one point on the shape through the center of the shape to a point directly across from it, unless otherwise specified. For polygonal shapes, the term "diameter" refers to the greatest possible distance measured from a vertex of a polygon through the center of the face to the vertex on the opposite side, unless otherwise specified.

As used herein, "mesoporous" materials are those containing mesopores, that is, pores with a diameter between 2 to 50 nm. As used herein, "microporous" materials are those containing micropores, that is, pores with a diameter less than 2 nm. On the other hand, "macroporous" materials are those containing macropores, that is, pores with a diameter greater than 50 nm. A material which possesses two or more types of pore sizes (e.g., micropores and mesopores) is said to be a "hierarchical" material in the present disclosure.

Catalyst

The present disclosure provides a hydrodesulfurization catalyst useful for desulfurizing hydrocarbon feedstocks. The hydrodesulfurization catalyst disclosed herein is easy to manufacture, is remarkably thermally stable under hydrodesulfurization temperature conditions, and possesses high desulfurization activity owing, in part, to the homogenous dispersion of the catalytically active metals on the catalyst support.

The present disclosure thus provides a hydrodesulfurization catalyst comprising, consisting essentially of, or consisting of a catalyst support that includes zeolite doped with a graphene material, and catalytic metals homogenously disposed on the catalyst support, the catalytic metals being molybdenum and a promoter selected from cobalt and nickel.

Catalyst Support

A catalyst support is a material, usually a solid with a high surface area, to which a catalyst(s) is affixed. The reactivity of heterogeneous catalyst and nanomaterial based catalysts occurs at the surface atoms. Thus, great effort is made herein to maximize the surface of a catalyst by evenly distributing it over the support. The support may be inert or may participate in the catalytic reactions. The catalyst support herein influences the physical characteristics and performance of the hydrodesulfurization catalysts.

The catalyst support of the present disclosure generally contains a zeolite doped with a graphene material.

Zeolite

In preferred embodiments, the catalyst support is made predominantly of a zeolite. Zeolites are microporous aluminosilicate minerals that may be found in nature or synthesized. Elementary building units of zeolites are $SiO_4$ and $AlO_4$ tetrahedra. Adjacent tetrahedra are linked at their corners via a common oxygen atom, which results in an inorganic macromolecule with a three-dimensional framework. The three-dimensional framework of a zeolite also comprises channels, channel intersections, and/or cages having dimensions in the range of 0.1-10 nm, preferably 0.2-5 nm, more preferably 0.3-2 nm. Water molecules may be present inside these channels, channel intersections, and/or cages.

Zeolite(s) that may be used herein include, but are not limited to, zeolites with a zeolite framework of, or similar to, amicite, ammonioleucite, analcime, barrerite, brewsterite, bellbergite, bikitaite, boggsite, chabazite, chiavennite, clinoptilolite, cowlesite, dachiardite, edingtonite, epistilbite, erionite, faujasite, ferrierite, garronite, gaultite, gismondine, gmelinite, gobbinsite, gonnardite, goosecreekite, gottardiite, harmotome, heulandite, hsianghualite, kalborsite, laumontite, leucite, lévyne, lovdarite, marciopaite, mazzite, merlinoite, mesolite, montesommaite, mordenite, mutinaite, nabesite, natrolite, offretite, pahasapaite, paranatrolite, parthéite, paulingite, perlialite, phillipsite, pollucite, roggianite, scolecite, stellerite, stilbite, terranovaite, tetranatrolite, thomsonite, tschernichite, tschortnerite, tvedalite, wairakite, weinebeneite, willhendersonite, yugawaralite, and combinations thereof, with specific mention being made to zeolite A, zeolite X, zeolite Y, zeolite ZK-5, zeolite beta, zeolite ZK-4, SAPO-34, AlPO, zeolite ZSM-5 ("Zeolites Socony Mobil-5" also called more simply, ZSM-5), ZSM-11, ZSM-12, ZSM-20, ZSM-23, ZSM-35, ZSM-38, ZSM-50, and combinations thereof.

In some embodiments, the zeolite is a faujasite-type zeolite, which is a mineral group in the zeolite family of silicate minerals consisting of faujasite-Na, faujasite-Mg and faujasite-Ca. They all share the same basic formula: $(Na_2,Ca,Mg)_{3.5}[Al_7Si_{17}O_{48}] \cdot 32(H_2O)$ by varying the amounts of sodium, magnesium and calcium. Depending on the silica-to-alumina ratio of their framework, faujasite zeolites are divided into X and Y-type zeolites. In preferred embodiments, the zeolite is a Y-type zeolite (Y-zeolite), for example ZEOLITE Y NIST RM 8850, available from Sigma-Aldrich.

In Y-type zeolites, the silica and alumina tetrahedral are connected by oxygen linkages. Y-zeolites have pores, formed by a 12-membered ring, with a relatively large diameter of 7.4 Å. The inner cavity has a diameter of 12 Å and is surrounded by 10 sodalite cages. Unmodified Y-zeolite has a void fraction of 48% and a Si/Al ratio of 2.43. In order to impart thermal and hydrothermal stability, the Y-zeolite may be subjected to treatment to knock off some framework alumina (one of these routes is steaming at high temperature). The Y-zeolite thus may have a Si/Al ratio of at least 2.43:1, preferably at least 2.5:1, preferably at least 2.6:1, preferably at least 2.7:1, preferably at least 2.8:1, preferably at least 2.9:1, preferably at least 3.0:1, preferably at least 3.1:1, preferably at least 3.2:1, and less than 4.0:1, preferably less than 3.9:1, preferably less than 3.8:1, preferably less than 3.7:1, preferably less than 3.6:1, preferably less than 3.5:1, preferably less than 3.4:1. In some embodiments, the zeolite is a dealuminated Y-zeolite having a Si/Al ratio of 4:1 or more. The dealuminated Y-zeolite, with a higher framework Si/Al ratio, has stronger acid sites (isolated acid sites) and is thermally and hydrothermally more stable and is thus called ultrastable Y-zeolite (USY-zeolite).

In preferred embodiments, the only zeolite material present in the catalyst support (and thus the hydrodesulfurization catalyst) is a Y-zeolite. Alternatively, the catalyst support may be formed from a mixed zeolite framework (comprises two or more different zeolite materials). When the zeolite is a mixed zeolite variety, it is preferably made of Y-zeolite plus one or more other zeolite types, such as those disclosed previously. In some embodiments, the catalyst support (and thus the hydrodesulfurization catalyst) is substantially free of amorphous aluminosilicate materials.

In some embodiments, the zeolite is present in the catalyst support in an amount of 80 to 99.9 wt. %, preferably 85 to 99.9 wt. %, preferably 90 to 99.8 wt. %, preferably 95 to 99.7 wt. %, preferably 96 to 99.6 wt. %, preferably 97 to 99.5 wt. %, based on a total weight of the catalyst support.

Graphene material

The zeolite of the present disclosure is preferably doped with a graphene material. It has been found that the inclusion of the graphene material enhances the activity of the hydrodesulfurization catalyst. Without being bound by theory, it is believed that the graphene material improves the physico-chemical properties of the hydrodesulfurization catalysts (i.e., beneficially influences the surface area, pore size, pore volume, hierarchy factor, etc.), enhances the thermal stability of the hydrodesulfurization catalysts, and improves dispersion of the catalytic metals over the catalyst support.

In some embodiments, the graphene material is present in the catalyst support in an amount of 0.1 to 0.5 wt. %, preferably 0.15 to 0.45 wt. %, preferably 0.2 to 0.4 wt. %, preferably 0.25 to 0.38 wt. %, preferably 0.3 to 0.36 wt. %, preferably 0.31 to 0.35 wt. %, preferably 0.32 to 0.33 wt. %, based on a total weight of the catalyst support. In preferred embodiments, the graphene material is present in the catalyst support in the amounts described above, with the remainder of the catalyst support being composed of the zeolite, preferably zeolite-Y.

Graphene is an allotrope of carbon in the form of a two-dimensional, atomic-scale hexagonal lattice in which one atom forms each vertex and is the basic structural element of other allotropes including graphite, charcoal, carbon nanotubes and fullerenes. Structurally, graphene is a sheet of six membered carbon rings that do not form a closed surface. Its carbon atoms are densely packed in a regular atomic-scale "chicken wire" (hexagonal) pattern. Each atom has four bonds, one σ-bond with each of its three neighbors and one π-bond that is oriented out of the plane. Graphene's hexagonal lattice can be regarded as two interleaving triangular lattices. Graphene's stability is due to its tightly packed carbon atoms and each carbon atom in a graphene sheet having a $sp^2$ orbital hybridization and delocalized electrons present at opposite surfaces of the graphene sheet. The $sp^2$ hybridization is a combination of orbitals S, $P_x$ and $P_y$ that constitute the σ-bond, the final $P_z$ electron makes up the π-bond. The π-bonds hybridize together to form the π-band and the π*-band. These bands are responsible for most of graphene's notable electronic properties, via the half-filled band that permits free-moving electrons. Graphene is a zero-gap semiconductor. Graphene is also a form of carbon (or solid material) in which every atom is available for chemical reaction from two sides (due to the 2D structure).

In some embodiments, the graphene material is pristine graphene, meaning graphene which has not been chemically modified so as to possess oxygen functional groups (e.g., hydroxyl groups, carboxyl groups, epoxy groups etc.). Pristine graphene is thus a pure carbonaceous material containing only carbon.

In some embodiments, the graphene material is reduced graphene oxide (rGO), which is a graphene-like material but which contains defects/aromatic network interruptions not present in pristine graphene. Reduced graphene oxide typically contains only minor amounts of oxygen (which are not reduced during the reduction process), with a C/O ratio of in the range of 5 to 200, preferably 10 to 180, preferably 20 to 160, preferably 30 to 140, preferably 40 to 120. Reduced graphene oxide which contains only minor amounts of oxygen (e.g., C/O ratio of 200) is chemically similar to pristine graphene, but possesses different properties due to its interrupted aromatic network/surface defects.

In preferred embodiments, the graphene material is graphene oxide. Graphene oxide is a compound of carbon, oxygen, and hydrogen in variable ratios, obtained by oxidation of graphene/graphite materials. Graphene oxide possess oxygen functional groups such as hydroxyl groups, carboxyl groups, epoxy groups, and phenolic groups. Graphene oxide layers are about 0.9 to 1.3 nm, preferably 1.0 to 1.2 nm, preferably 1.1 nm thick, and unlike pristine graphene, are buckled/puckered due to the presence of the oxygen defects. In some embodiments, the graphene oxide has a C/O ratio of 2.1 to 4, preferably 2.3 to 3.8, preferably 2.5 to 3.6, preferably 2.7 to 3.4, preferably 2.9 to 3.2. Therefore, in some embodiments, the graphene material comprises 25 to 47%, preferably 28 to 45%, preferably 30 to 40%, preferably 32 to 38%, preferably 34 to 36% of carbon atoms connected to an oxygen functional group (e.g., hydroxyl groups, carboxyl groups, epoxy groups etc.), based on a total number of carbon atoms. Graphene oxide is thus chemically distinct from pristine graphene and reduced graphene oxide at least in terms of oxygen content (e.g., C/O ratio of 2.1 to 2.9). In preferred embodiments, the graphene material is graphene oxide, and the hydrodesulfurization is substantially free of graphene (pristine or reduced graphene oxide).

When in the form of graphene oxide, the graphene material may chemically bond/coordinate to the zeolite, for example the oxygen functionality (e.g., carboxyl groups) present on the graphene oxide may participate in dative or ionic bonding to the Si and/or Al atoms of the zeolite.

In preferred embodiments, the graphene material is a sheet-like material (2D). In preferred embodiments, the catalyst support is substantially free of amorphous carbon materials such as activated carbon, carbon black, carbon fiber etc. In preferred embodiments, the catalyst support is substantially free of cylindrical or tubular carbonaceous materials such as carbon nanotubes, including both single-wall and multi-wall carbon nanotubes, and other 3-dimensional carbon materials such as 3D carbon fibers.

A ratio of the zeolite to the graphene material in the catalyst support may range from 160:1 to 999:1, preferably 180:1 to 900:1, preferably 200:1 to 800:1, preferably 220:1 to 700:1, preferably 240:1 to 600:1, preferably 260:1 to 500:1, preferably 280:1 to 400:1, preferably 300:1 to 350:1, preferably 320:1.

The catalyst support used herein may have a particulate form. In some embodiments, the catalyst support is in the shape of spheres, rods, cylinders, polygons (e.g., rectangles, triangles, pentagon, hexagon), prisms, disks, platelets, flakes, cubes, cuboids, or globular particles (i.e. generally globe shaped), preferably platelets, flakes, or globular particles. In some embodiments, the catalyst support has an average particle size of 0.1 to 5 µm, preferably 0.2 to 4 µm, preferably 0.3 to 3 µm, preferably 0.4 to 2 µm, preferably 0.5 to 1 µm, preferably 0.6 to 0.8 µm.

The hydrodesulfurization catalyst of the present disclosure may contain 70 to 94 wt. %, preferably 72 to 92 wt. %, preferably 74 to 90 wt. %, preferably 76 to 88 wt. %, preferably 78 to 86 wt. %, preferably 80 to 84 wt. % of the catalyst support, based on a total weight of the hydrodesulfurization catalyst.

Other support materials which may be optionally included in the catalyst support include, but are not limited to, carbonaceous materials (other than the graphene material), alumina, silica, silica-alumina (including conventional silica-alumina, silica-coated alumina, and alumina-coated silica, such as amorphous silica-alumina), titania, zirconia, magnesia, thoria, boria, cationic clays or anionic clays such as saponite, bentonite, kaoline, sepiolite or hydotalcite, and the like. In preferred embodiments, the catalyst support is substantially free of such other support materials.

Catalytic metals

The hydrodesulfurization catalyst also includes, as catalytic metals, one or more primary catalytic metals of group 6 elements and one or more promoters of group 9 or group 10 elements. The weight ratio of the primary catalytic metal to the promoter may range from 1.5:1 to 5:1, preferably 2:1 to 4.5:1, preferably 2.5:1 to 4:1, preferably 3:1 to 3.5:1.

Suitable primary catalytic metals may include chromium, molybdenum, and/or tungsten. In some embodiments, the hydrodesulfurization catalyst includes molybdenum. In preferred embodiments, the primary catalytic metal is molybdenum, i.e., molybdenum is the only primary catalytic metal present (i.e., no other group 6 element is present in the hydrodesulfurization catalyst).

In some embodiments, the hydrodesulfurization catalyst contains 5 to 20 wt. %, preferably 8 to 19 wt. %, preferably 10 to 18 wt. %, preferably 12 to 17 wt. %, preferably 14 to 16 wt. %, preferably 15 wt. % of the primary catalytic metal (e.g., molybdenum), based on a total weight of the hydrodesulfurization catalyst.

Suitable promoters may include cobalt, rhodium, iridium, nickel, palladium, and platinum. In some embodiments, the promoter is either cobalt or nickel. In preferred embodiments, the promoter is either cobalt or nickel, and no other group 9 or group 10 elements are present.

In some embodiments, the hydrodesulfurization catalyst contains 1 to 6 wt. %, preferably 2 to 5.8 wt. %, preferably 3 to 5.6 wt. %, preferably 4 to 5.4 wt. %, preferably 5 to 5.2 wt. % of the promoter, preferably of either cobalt or nickel, based on a total weight of the hydrodesulfurization catalyst.

In preferred embodiments, the promoter is cobalt. In other preferred embodiments, the promoter is nickel.

In some embodiments, the hydrodesulfurization catalyst is a cobalt molybdenum catalyst (CoMo). In some embodiments, the hydrodesulfurization catalyst is a nickel molybdenum (NiMo) catalyst. In preferred embodiments, the catalyst support consists of the zeolite doped with the graphene material, and the hydrodesulfurization catalyst consists of the catalyst support, molybdenum (as the primary catalytic metal), and either cobalt or nickel (as the promoter). In some embodiments, the hydrodesulfurization catalyst is substantially free of metal carbides and metal nitrides.

The catalytic metals (i.e., the primary catalytic metal and the promoter) are disposed on the catalyst support. As used herein, "disposed on" describes catalytic materials being deposited on, dispersed in, or impregnated in the support material. The catalytic metals may be affixed to the catalytic support in any reasonable manner, such as physisorption, chemisorption, or mixtures thereof. In preferred embodiments, the catalytic metals (e.g., nickel and molybdenum) are homogeneously/uniformly disposed on (e.g., distributed throughout) the catalyst support, where the concentration of the catalytic metals differs by no more than 5%, by no more than 4%, by no more than 3%, by no more than 2%, by no more than 1% by weight at any given cross section throughout the hydrodesulfurization catalyst. The catalytic metals (i.e., the primary catalytic metal and the promoter) and their distributions on the catalytic support may be identified, for example, by electron dispersive X-ray spectrometry (EDS or EDX) mapping. The catalytic metals may be present as elemental metals, metal oxides, or metal sulfides. For example, in some embodiments, the catalytic metals are metal oxides (e.g., oxides of Co and Mo or oxides of Ni and Mo). In some embodiments, the hydrodesulfurization catalyst is pre-sulfided or sulfided in situ during hydrodesulfurization, whereby any elemental or oxides of the catalytic metals present on the catalyst support are converted into sulfide form. In preferred embodiments, the catalytic metals are in the form of metal sulfides (e.g., sulfides of Co and Mo or sulfides of Ni and Mo).

In some embodiments, greater than 10% of the surface area (i.e. surface and pore spaces) of the catalyst support is covered by catalytic metals (i.e., the primary catalytic metal and the promoter), preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%.

Figure 6A:
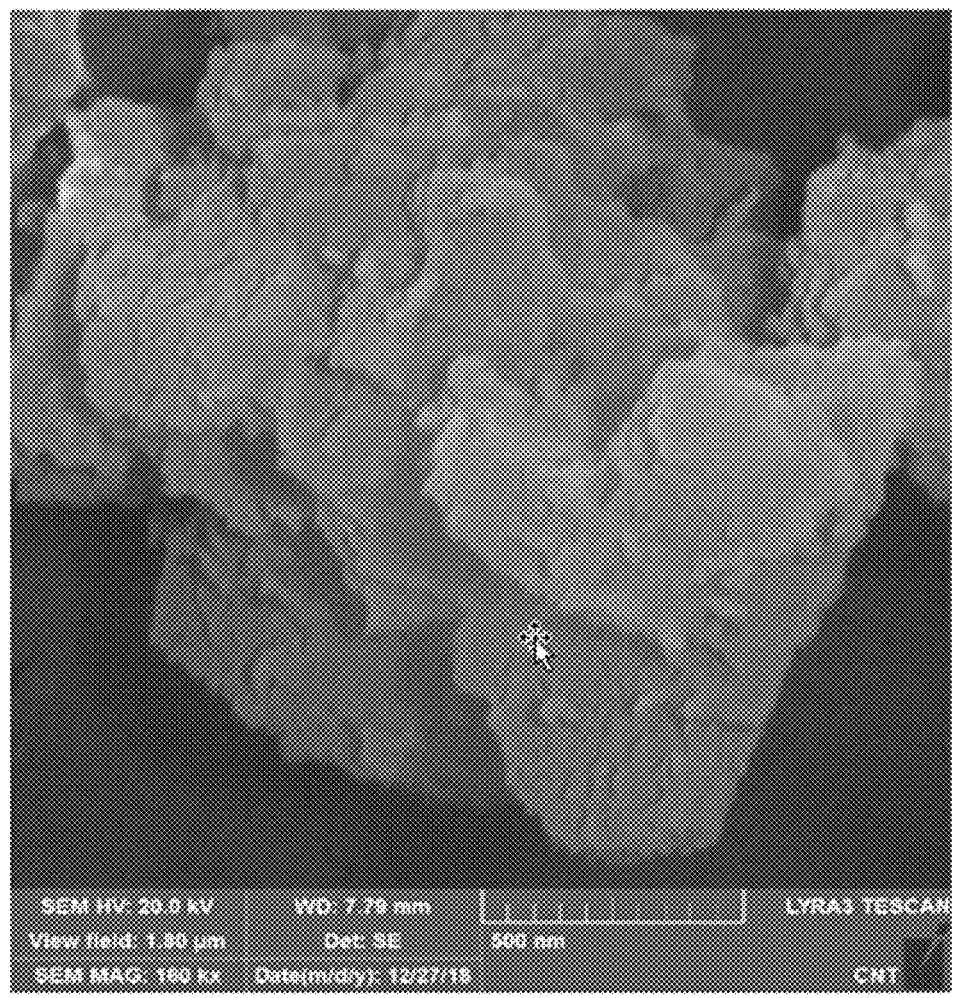
FIGS. 6A-6H illustrate SEM images for ZMI (FIGS. 6A-6B), ZMC (FIGS. 6C-6D), ZGMI (FIGS. 6E-6F) and ZGMC (FIGS. 6G-6H)
Figure 6B:
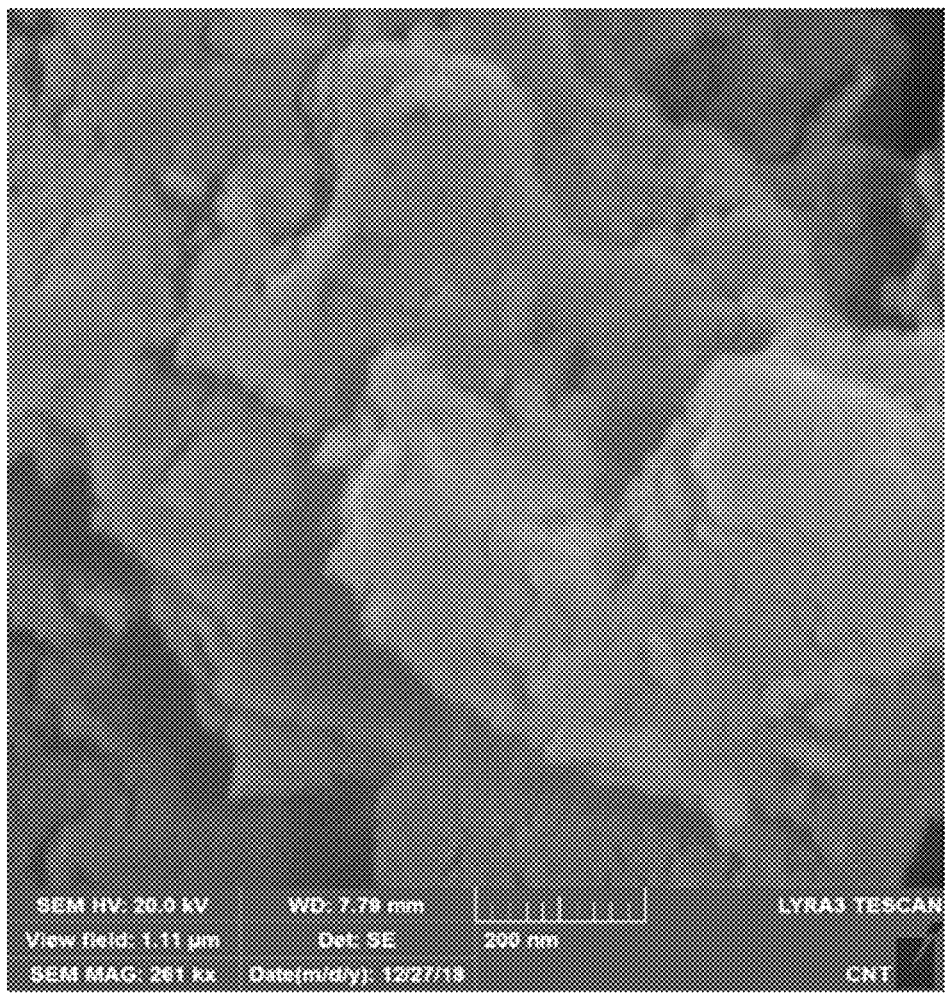
Figure 6C:
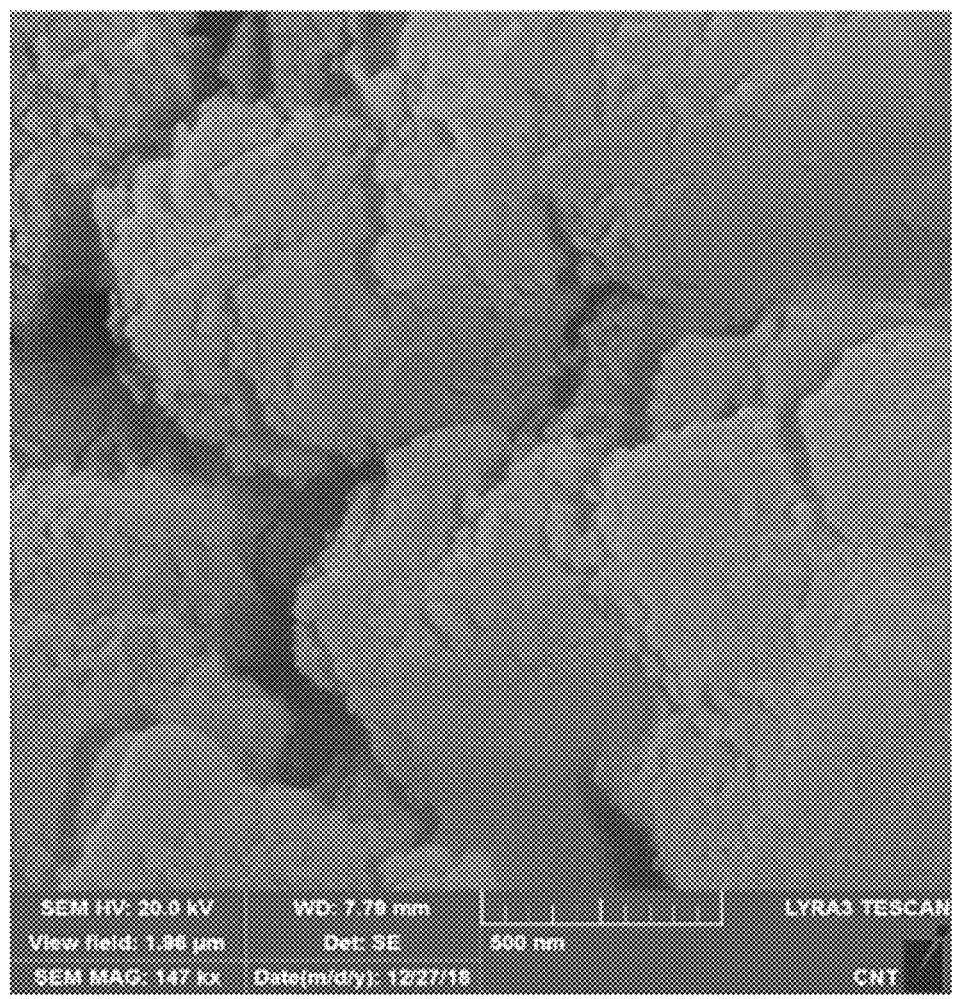
Figure 6D:
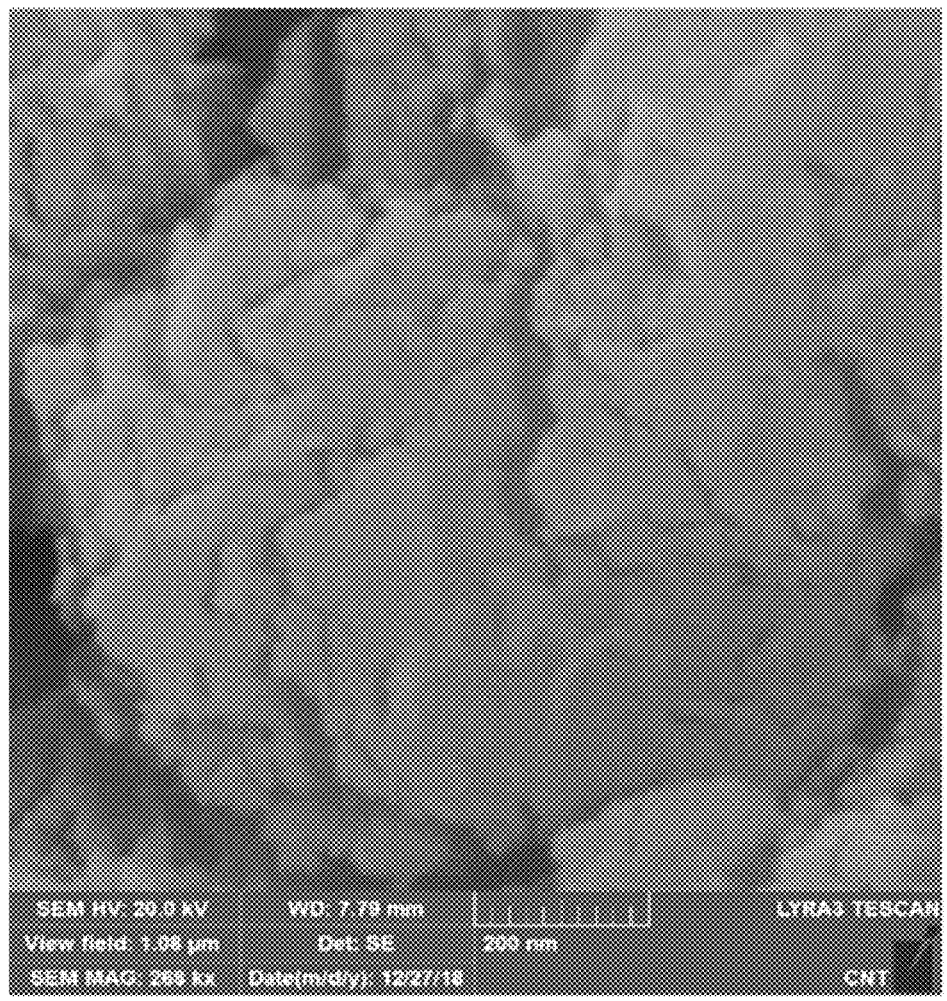
Figure 6E:
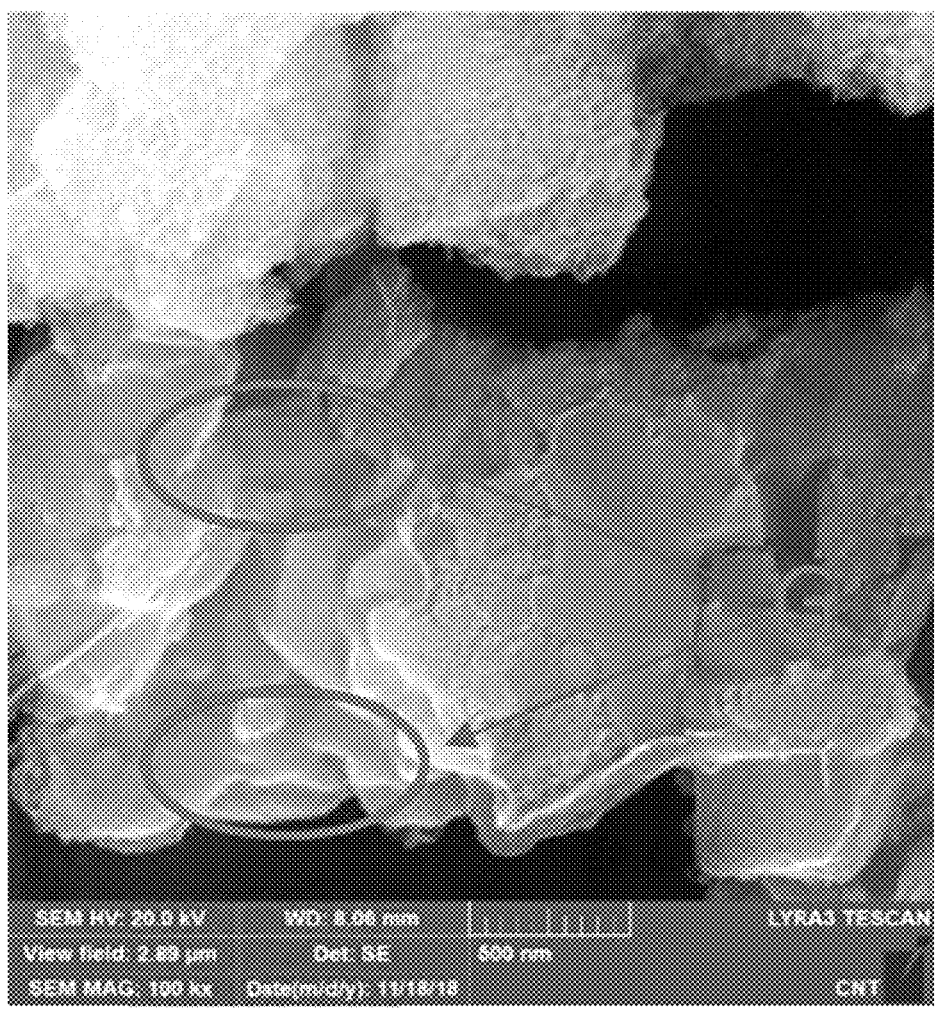
Figure 6F:
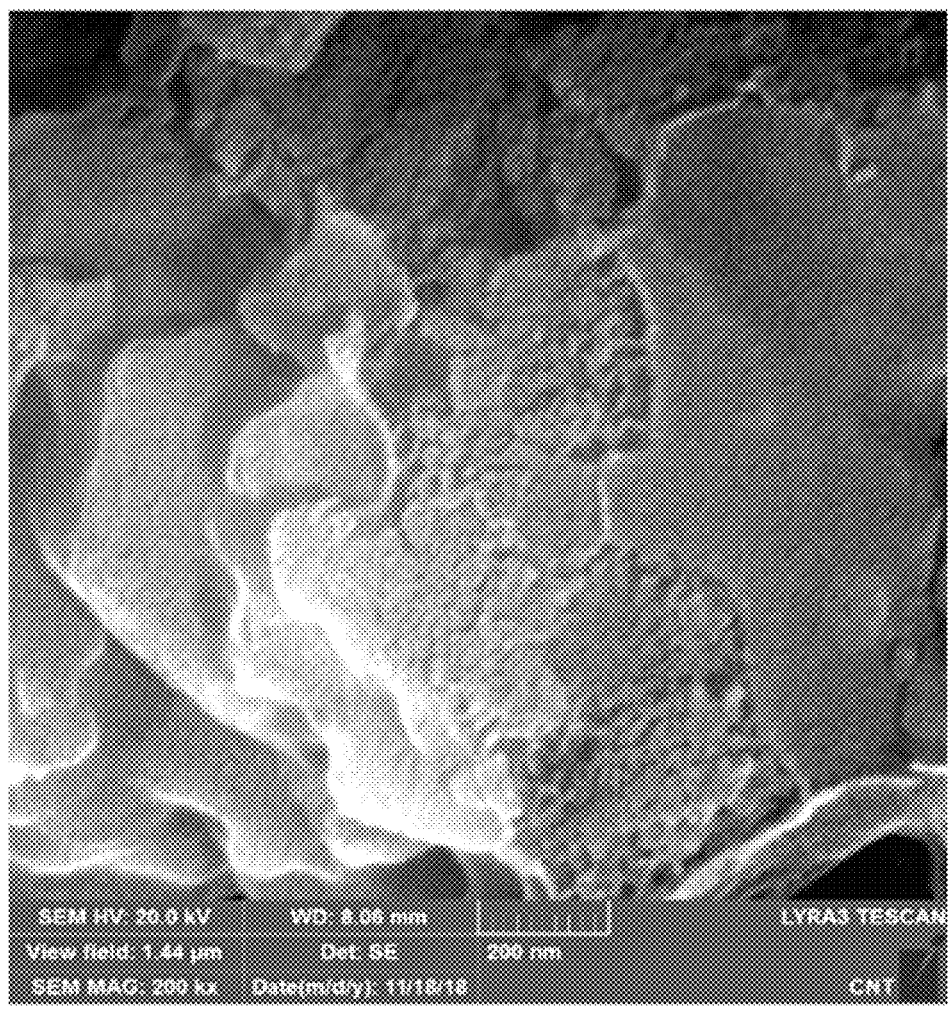
Figure 6G:
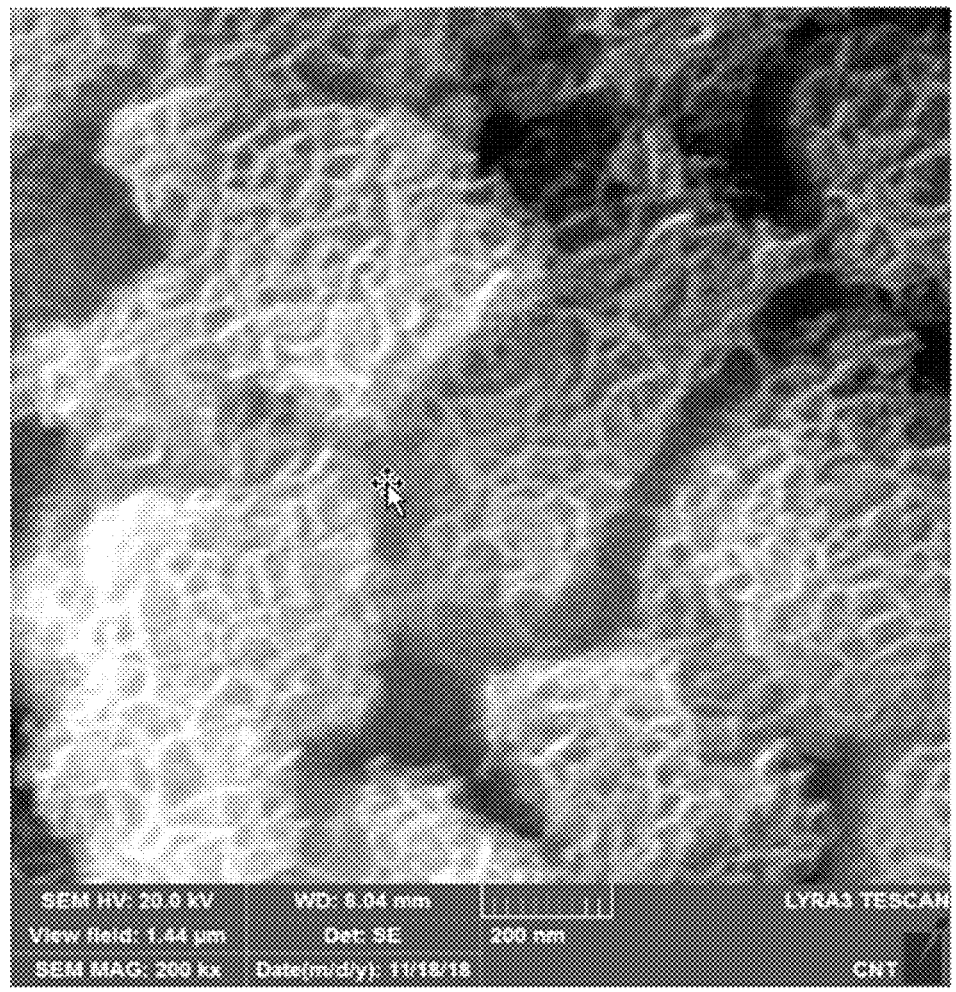
Figure 6H:
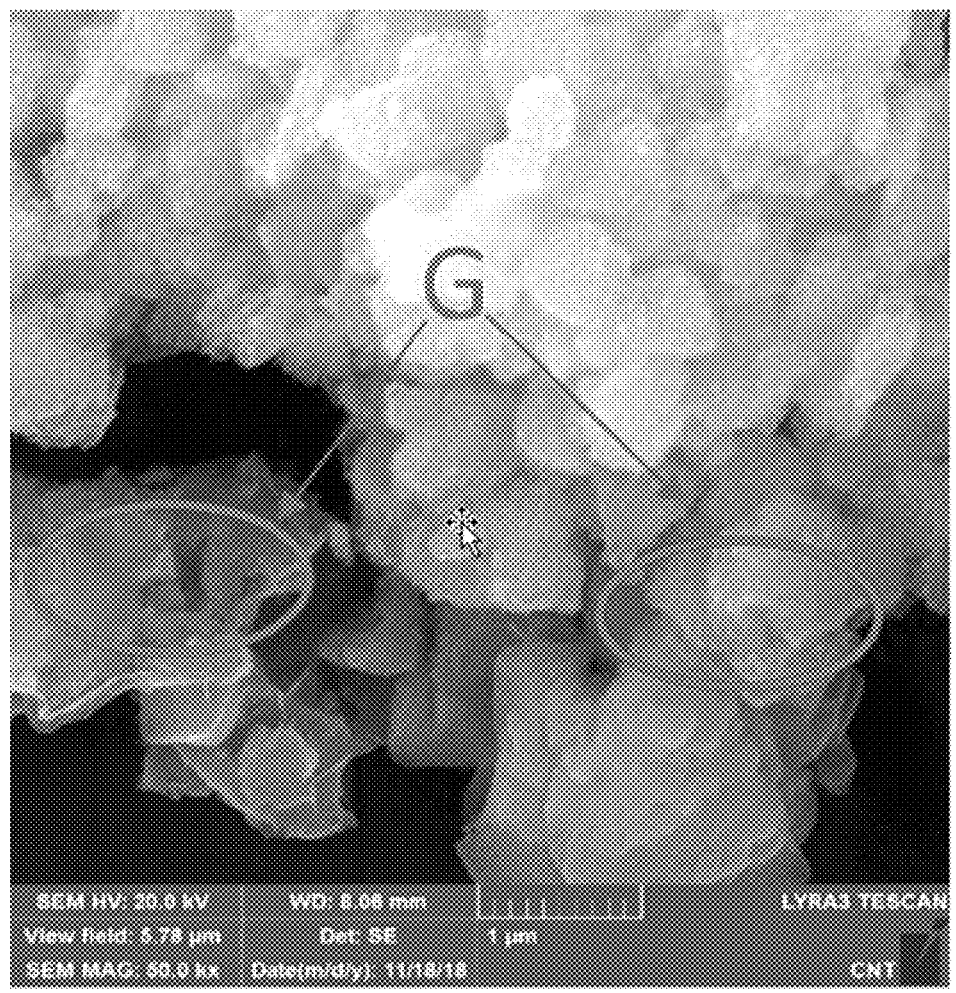
Figure 7A:
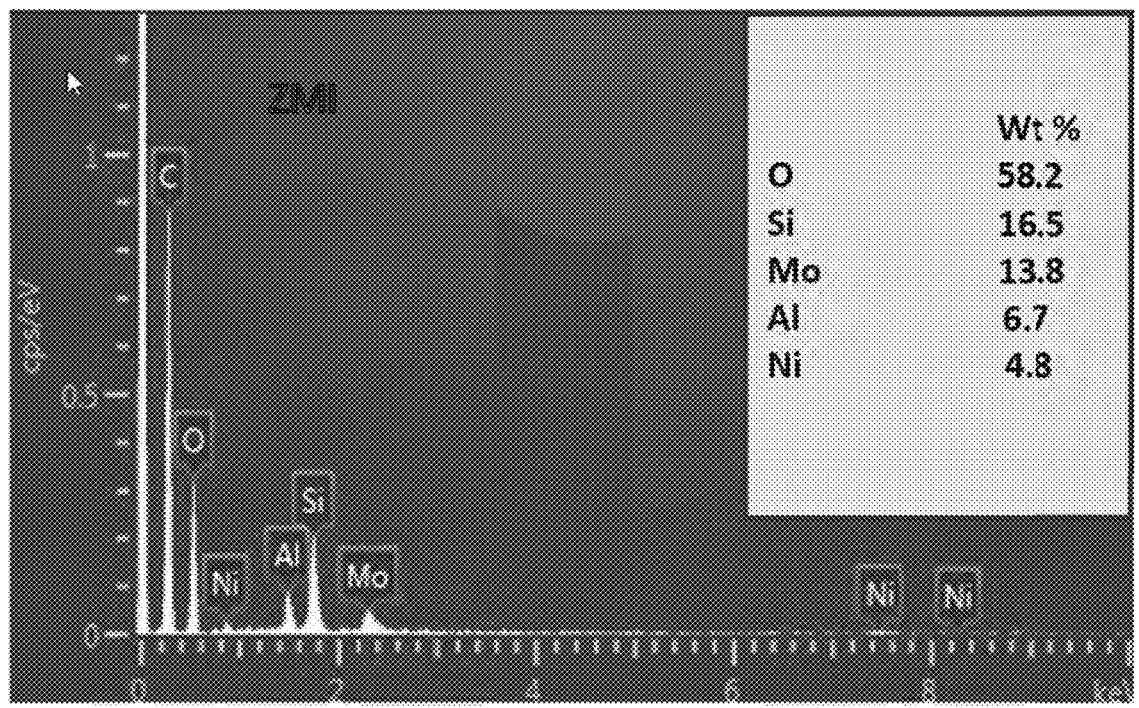
FIGS. 7A-7D illustrate the EDX analysis for ZMI (7A), ZMC (7B), ZGMI (7C), and ZGMC (7D)
Figure 7B:
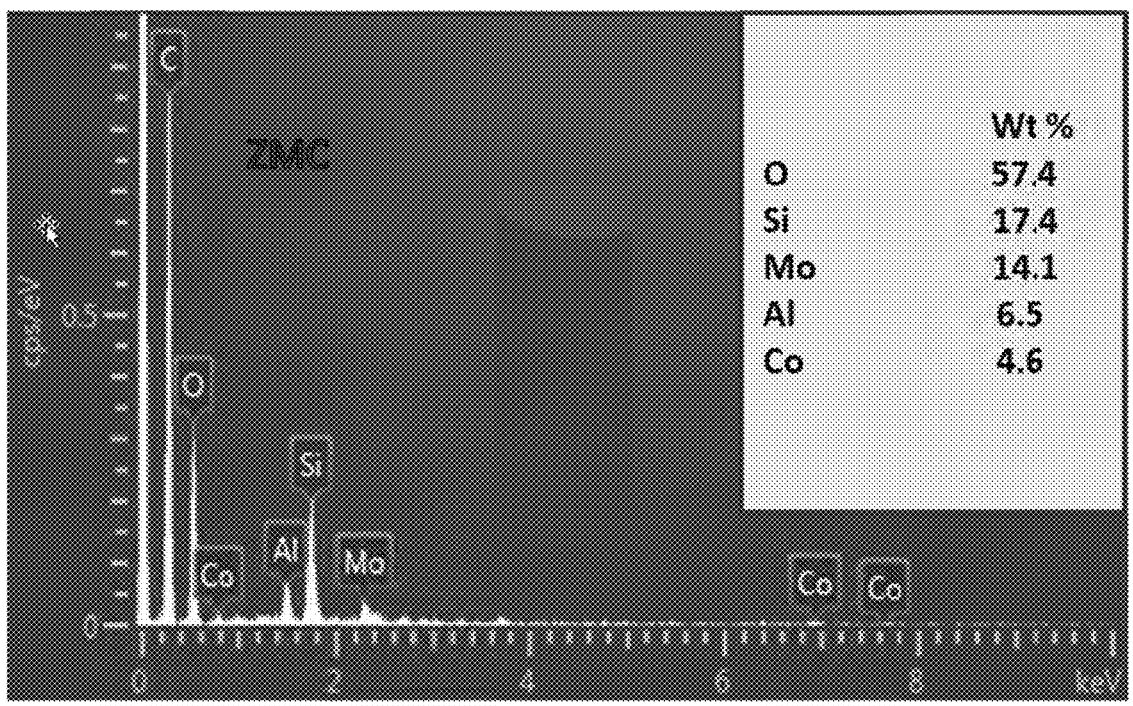
Figure 7C:
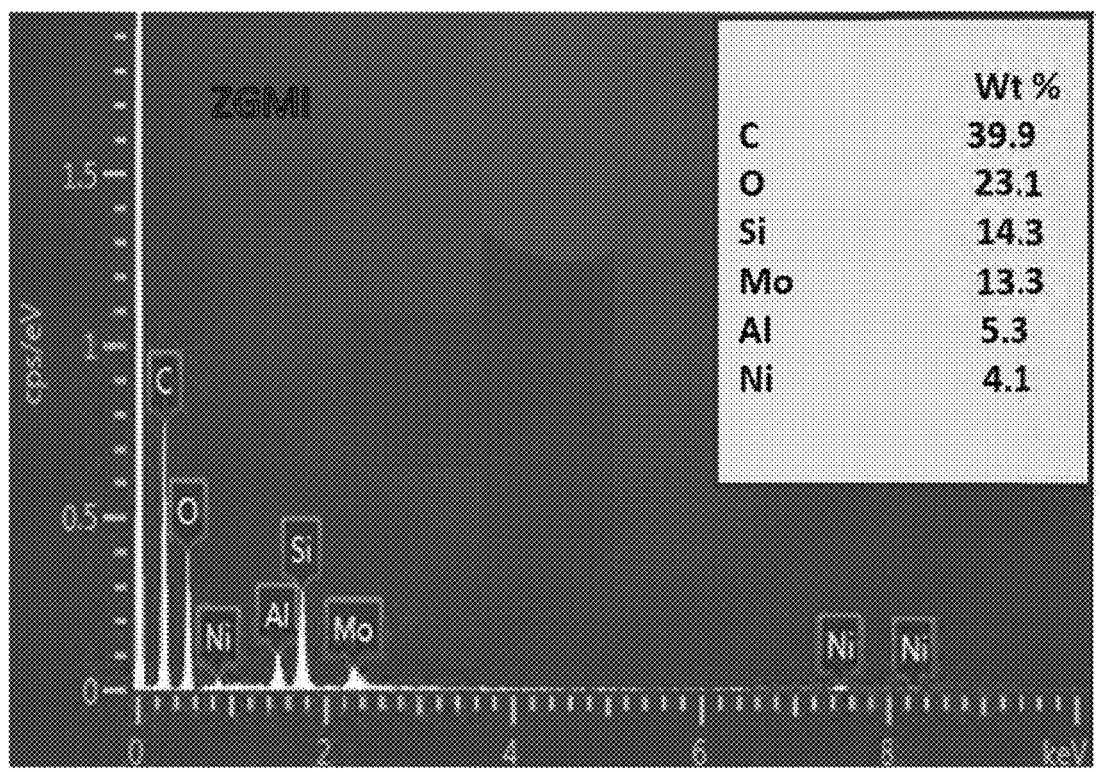
Figure 7D:
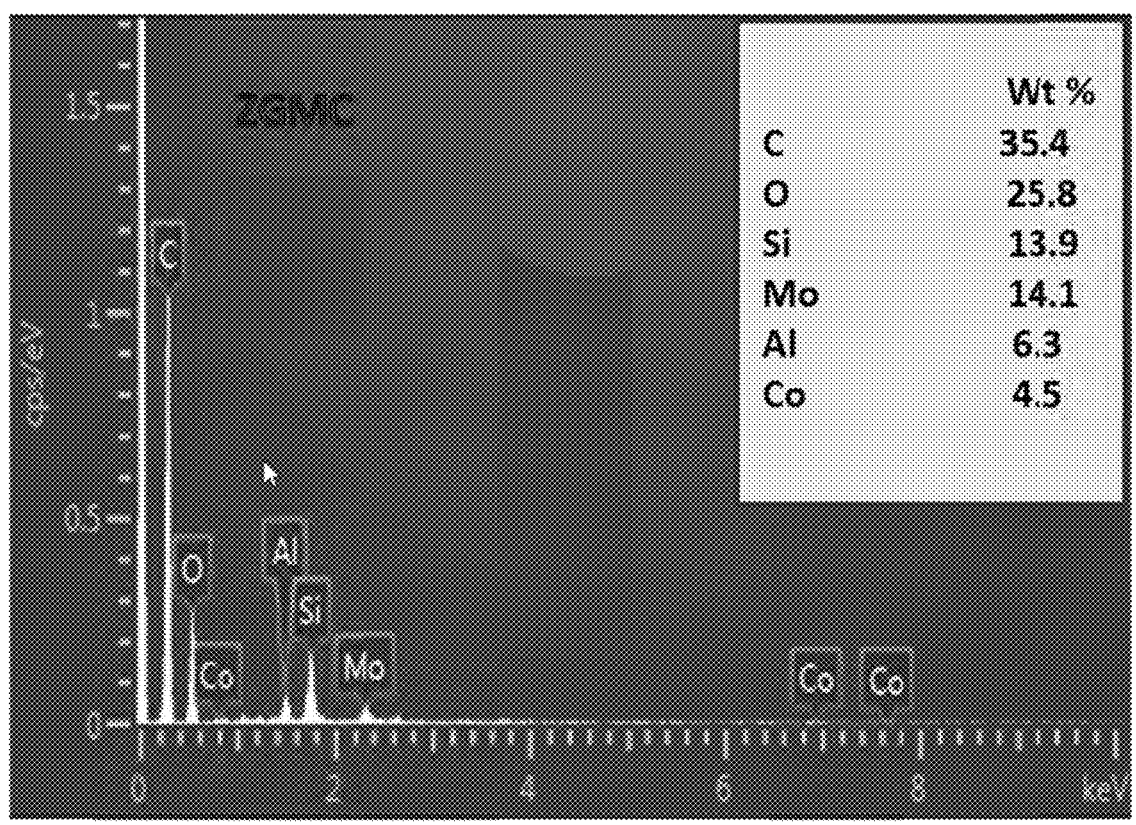
Figure 8A:
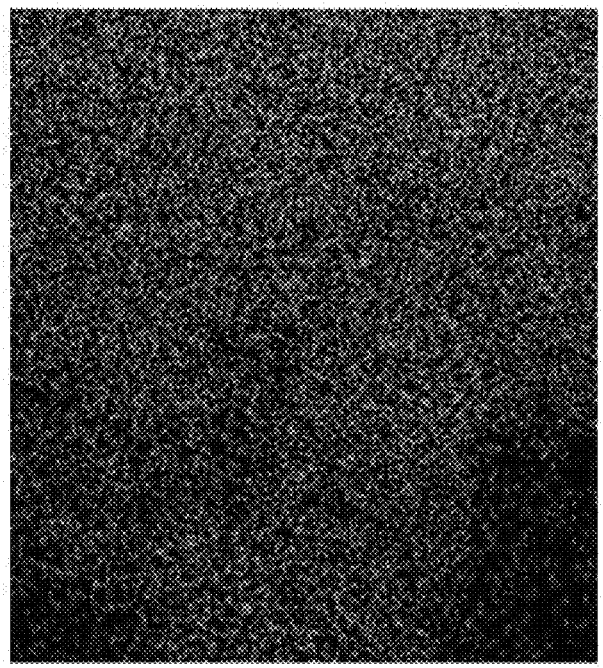
FIGS. 8A-8F illustrate the EDX mapping of the catalyst ZGMI for elements of Si (8A), C (8B), O (8C), Al (8D), Mo (8E), and Ni (8F)
Figure 8B:
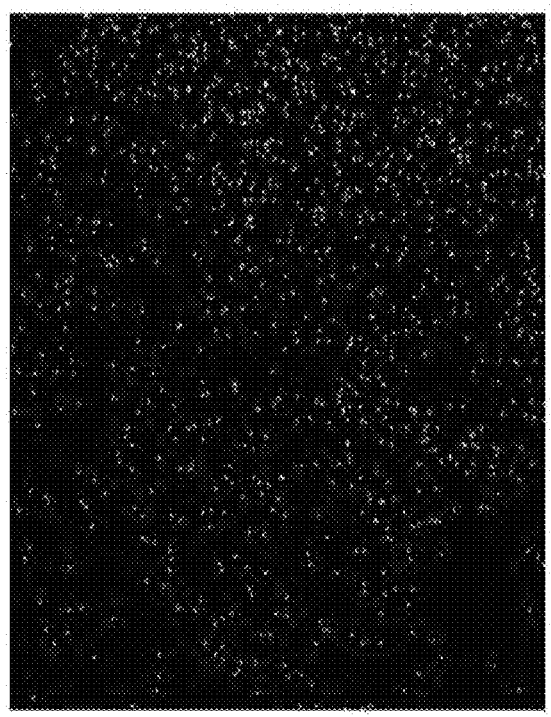
Figure 8C:
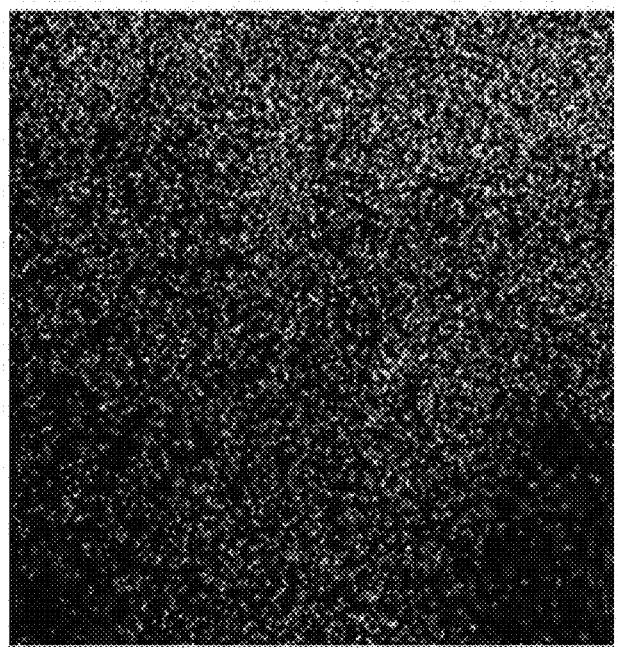
Figure 8D:
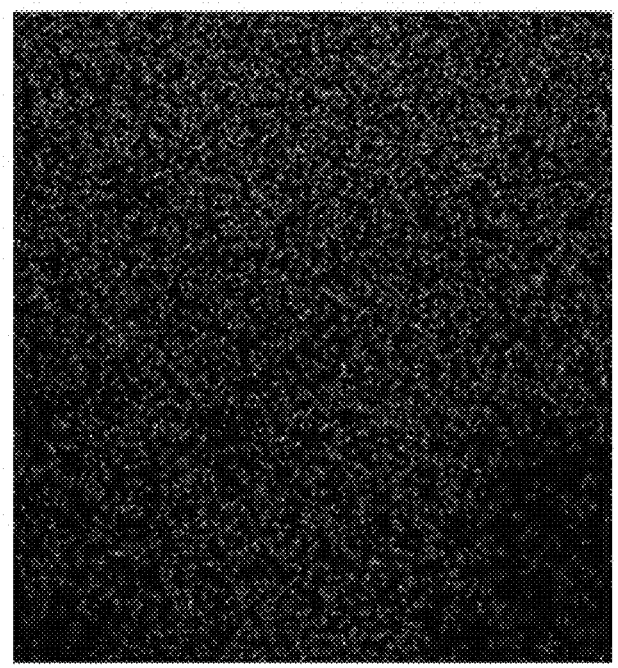
Figure 8E:
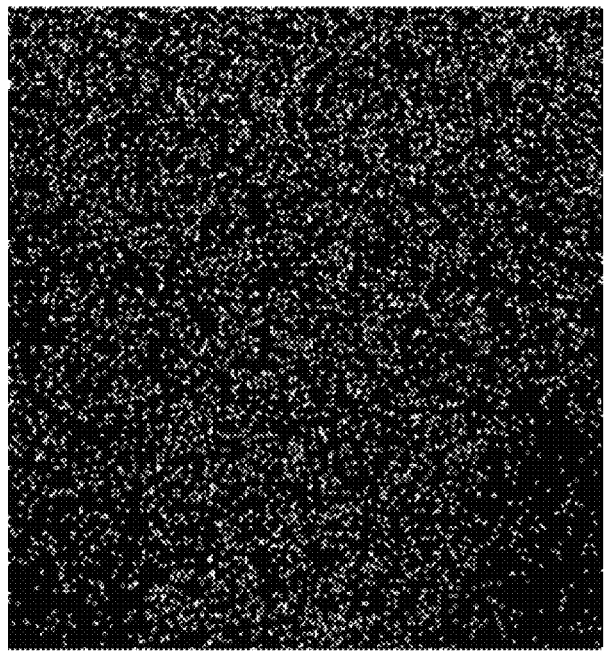
Figure 8F:
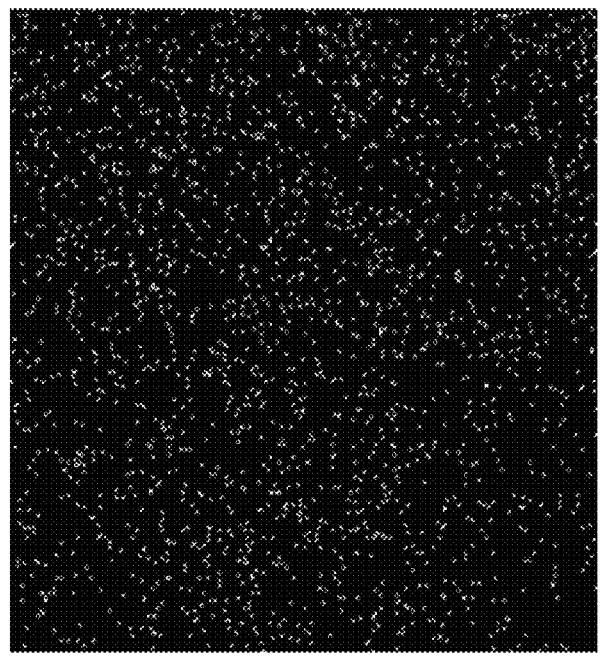

The hydrodesulfurization catalyst of the present disclosure may have a particulate form, with particles in the shape of spheres, rods, cylinders, polygons (e.g., rectangles, triangles, pentagon, hexagon), prisms, disks, platelets, flakes, cubes, cuboids, or globular particles (i.e. generally globe shaped), preferably platelets, flakes, or globular particles, preferably globular particles with a rippled/sponge-like/cellular morphology (see for example FIG. 6G) In some embodiments, the hydrodesulfurization catalyst has an average particle size of 0.1 to 5 µm, preferably 0.2 to 4 µm, preferably 0.3 to 3 µm, preferably 0.4 to 2 µm, preferably 0.5 to 1µm, preferably 0.6 to 0.8 µm.

The Brunauer-Emmet-Teller (BET) theory (S. Brunauer, P. H. Emmett, E. Teller, I Am. Chem. Soc. 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. Pore size (i.e., pore diameter), pore volume, and BET surface area are measured by gas adsorption analysis, preferably $N_2$ adsorption analysis (e.g. $N_2$ adsorption isotherms).

In some embodiments, the hydrodesulfurization catalyst contains mesopores. In some embodiments, the hydrodesulfurization catalyst contains micropores. In preferred embodiments, the hydrodesulfurization catalyst is a hierarchical material and contains both mesopores and micropores. In preferred embodiments, the hydrodesulfurization catalyst has pore channels which are regularly arranged, for example, a pore system of spherical cages connected tretrahedrally with four neighboring cages through windows formed by 12-linked tetrahedra, or a three-dimensional, 12-membered-ring pore system. While the hydrodesulfurization catalyst may contain regularly arranged pore channels based on the structure of the zeolite employed, the hydrodesulfurization catalyst is preferably in particulate form and is not in the form of a monolith structure (i.e., a support structure that contains many parallel channels or holes in a honeycomb structure which supports a catalytic metal), see for example U.S. Pat. No. 9,631,148B2—incorporated herein by reference in its entirety.

In some embodiments, the hydrodesulfurization catalyst has an average pore diameter of 3 to 3.8 nm, preferably 3.1 to 3.7 nm, preferably 3.2 to 3.6 nm, preferably 3.3 to 3.5 nm. In some embodiments, the hydrodesulfurization catalyst has a total pore volume of 0.25 to 0.30 m³/g, preferably 0.255 to 0.295 m³/g, preferably 0.22 to 0.29 m³/g, preferably 0.265 to 0.285 m³/g, preferably 0.27 to 0.28 m³/g.

In hierarchical catalysts, the introduction in mesopores is frequently coupled to a lowered micropore volume. The loss of microporosity is generally undesirable in zeolite containing catalysts. Hierarchy factor (HF) is an indicator of mesoporous surface area enhancement and corresponding decrease of the microporous volume and can be used to classify the hierarchical porous characteristics of any material, independent of the synthetic methodology used for their synthesis. Hierarchy factor (HF) is defined as:

$$HF = \frac{V_{micro}}{V_{total}} \times \frac{S_{meso}}{S_{BET}} \quad (1)$$

where $V_{micro}$ is the microporous volume, $V_{total}$ is the total pore volume, $S_{meso}$ is the mesoporous surface area, and $S_{BET}$ is the BET (total) surface area. A material with a high hierarchy factor would have a small decrease of microporosity at high mesoporous volume and thus advantageous catalytic properties. In preferred embodiments, the hydrodesulfurization catalyst has a hierarchy factor (HF) of 0.020 to 0.035, preferably 0.021 to 0.034, preferably 0.022 to 0.032, preferably 0.023 to 0.030, preferably 0.024 to 0.029, preferably 0.025 to 0.028, preferably 0.025 to 0.027.

In some embodiments, the hydrodesulfurization catalyst has a BET surface area of 290 to 350 m²/g, preferably 295 to 340 m²/g, preferably 298 to 330 m²/g, preferably 300 to 320 m²/g, preferably 301 to 315 m²/g, preferably 302 to 313 m²/g, preferably 304 to 311 m²/g, preferable 308 to 310.5 m²/g.

The hydrodesulfurization catalyst of the present disclosure may have a compressive modulus of 2 to 8 MPa, preferably 3 to 7 MPa, preferably 4 to 6 MPa, preferably 5 MPa, although hydrodesulfurization catalysts with a higher or lower compressive modulus may also be provided.

The hydrodesulfurization catalysts of the present disclosure are also stable at high temperatures (e.g., temperatures of up to 900° C.), and thus may remain active in applications requiring high temperatures, In some embodiments, the hydrodesulfurization catalysts have a percent weight loss of 15 to 20%, preferably 16 to 19.5%, preferably 17 to 19%, preferably 17.3 to 18.98%, when heated to a temperature of 900° C. This compares favorably to catalysts which are substantially the same except for that they do not include the graphene material (the zeolite component of the catalyst support is not doped with a graphene material), which experience a percent higher weight loss of 22.68 to 27.67% when subjected to the same high temperature conditions.

It has thus been found that the inclusion of the graphene material in the catalyst support improves the physico-chemical properties of the hydrodesulfurization catalysts (i.e., beneficially influences the surface area, pore size, pore volume, hierarchy factor, etc.), enhances the thermal stability of the hydrodesulfurization catalysts, and improves dispersion of the catalytic metals over the catalyst support, resulting in highly active hydrodesulfurization catalysts for the removal of sulfur from hydrocarbon feedstocks.

A Method of Making

The present disclosure also provides a method of producing the hydrodesulfurization catalyst. While any technique known by those of ordinary skill in the art may be used for synthesizing the hydrodesulfurization catalyst, impregnation techniques, preferably incipient wetness impregnation techniques may be used for impregnating the catalyst support with the catalytic metals described above for forming the hydrodesulfurization catalyst.

Catalyst Support Synthesis

The catalyst support is first provided. The catalyst support may be formed by mixing together the zeolite, the graphene material, water, an alcohol solvent, and optionally a polymeric dispersant to form a support mixture.

The support mixture may contain the following components in terms of weight percent relative to a total weight of the support mixture: the zeolite in an amount of 3 to 8 wt. %, preferably 4 to 7 wt. %, preferably 5 to 6 wt. %, preferably 5.5 to 5.6 wt. %; the graphene material in an amount of 0.01 to 0.03 wt. %, preferably 0.015 to 0.025 wt. %, preferably 0.017 to 0.02 wt. %, preferably 0.0175 to 0.018 wt. %; an alcohol solvent in an amount of 1 to 10 wt. %, preferably 3 to 9 wt. %, preferably 5 to 8 wt. %, preferably 6 to 7 wt. %; optionally a polymeric dispersant in an amount of 0.01 to 1 wt. %, preferably 0.05 to 0.8 wt. %, preferably 0.1 to 0.6 wt. %, preferably 0.15 to 0.4 wt. %, preferably 0.17 to 0.2 wt. %; with the balance being water, preferably 80 to 90 wt. % water, preferably 82 to 88 wt. % water, preferably 84 to 87 wt. % water, preferably 85 to 86 wt. % water.

Acceptable alcohol solvents may include, but are not limited to monoalcohols such as methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, and benzyl alcohol,; as well as polyalcohols such as ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, and pentaerythritol. Preferably, the alcohol solvent is methanol, ethanol, propanol, isopropanol, more preferably ethanol.

When used, suitable polymeric dispersants may include, but are not limited to, polyvinylpyrrolidone; polymaleates (e.g., homopolymers of maleic acid (HPMA)); polyacrylates (e.g., acylic acid homopolymer (PAA or HAA); sodium acrylate homopolymer); polymethacrylates; polyacrylamides; polysaccharides including modified polysaccharides (e.g., carboxymethyl inulin); amino acid-based polymers (e.g., polyaspartic acid (PASP) homopolymer and salts thereof); formaldehyde resins (e.g., melamine formaldehyde, urea-formaldehyde, phenol formaldehyde, etc.); epoxy resins; alkyl-phenol copolymers of polypropylene; polyethyleneimines (PEI) which may be oligomers or polymers with a repeating unit composed of an amine group and a two carbon aliphatic (—$CH_2CH_2$—) spacer, and may be linear polyethylene imines containing all secondary amines (with the exception of the terminal positions), or branched polyethylene imines containing primary, secondary and tertiary amino groups; alkylene oxide polymers such as polyethylene glycol, polypropylene glycol, polybutylene glycol, ethylene oxide (EO)/propylene oxide (PO) block copolymers including diblock and triblock (e.g., poloxamers) copolymers of alkylene oxides (e.g., EO-PO-EO or PO-EO-PO) with specific mention being made to POLOXAMER 407 available from Sigma-Aldrich, which is a triblock copolymer of a central hydrophobic block of polypropylene glycol flanked by two hydrophilic blocks of polyethylene glycol, and P123 POLOXAMER (i.e. P123), which is a symmetric triblock copolymer comprising poly(ethylene oxide) (PEO) and poly(propylene oxide) (PPO) in an alternating linear fashion, PEO-PPO-PEO, also known as PLURONIC P-123, available from Sigma-Aldrich. When employed, the polymeric dispersant is preferably polyvinylpyrrolidone.

Mixing may occur via stirring, shaking, swirling, sonicating, blending, or by otherwise agitating to form the support mixture. In some embodiments, the support mixture is stirred by a magnetic stirrer or an overhead stirrer. In some embodiments, the support mixture is subjected to ultrasonication, for example, via an ultrasonic bath or an ultrasonic probe. The support mixture may be mixed for any time suitable to evenly distribute the components throughout the support mixture, typically for 10 to 90 minutes, preferably 30 to 70 minutes, preferably 60 minutes.

The support mixture may then be optionally heated to 40 to 150° C., preferably 60 to 140° C., preferably 80 to 130° C., preferably 100 to 120° C., preferably 110° C., or otherwise to the reflux temperature of the support mixture, with continuous mixing for 1 to 10 hours, preferably 2 to 9 hours, preferably 3 to 8 hours, preferably 4 to 7 hours, preferably 5 to 6 hours.

Next, the support mixture may be filtered using any filtration technique known to those of ordinary skill in the art to obtain a filtrate, and the filtrate may be subsequently dried, for example under vacuum, or under heating conditions of 70 to 110° C., preferably 80 to 100° C., preferably 90 to 95° C. to obtain the catalyst support.

Impregnation

The catalyst support may be impregnated, preferably impregnated via the incipient wetness technique, by adding an aqueous solution comprising a salt of the primary catalytic metal (e.g., a molybdenum salt) and a salt of the promoter (e.g., a cobalt salt or a nickel salt) to a suspension of the catalyst support in water to form a catalyst mixture.

The catalyst support may be suspended in water to form a suspension having 1 to 20 wt. %, preferably 2 to 15 wt. %, preferably 3 to 10 wt. %, preferably 4 to 8 wt. %, preferably 5 to 6 wt. % of the catalyst support. This suspension may be optionally stirred and heated, for example, at a temperature of 70 to 110° C., preferably 80 to 100° C., preferably 90 to 95° C.

The aqueous solution may be prepared my combining a salt of the primary catalytic metal (e.g., a molybdenum salt) and a salt of the promoter (e.g., a cobalt salt or a nickel salt) in amounts suitable for providing the hydrodesulfurization catalyst with the quantities of catalytic metals as described above. In preferred embodiments, the salt of the primary catalytic metal is a molybdenum salt, preferably a molybdenum(VI) salt. In preferred embodiments, the salt of the promoter is a cobalt salt or a nickel salt.

Exemplary molybdenum salts include, but are not limited to, ammonium heptamolybdate(VI), ammonium molybdate (VI), ammonium orthomolybdate(VI), ammonium phosphomolybdate, ammonium tetrathiomolybdate, sodium molybdate(VI), lithium molybdate(VI), molybdenum(VI) dichloride dioxide, bis(acetylacetonato)dioxomolybdenum (VI), and molybdenumhexacarbonyl, including hydrates thereof and mixtures thereof. In some embodiments, a molybdenum salt having a different oxidation state, such as +2 (e.g. molybdenum(II) carboxylates), +3 (e.g. molybdenum(III) chloride), +4 (e.g. molybdenum(IV) carbonate), and +5 (e.g. molybdenum(V) chloride), may be used.

Exemplary nickel salts include, but are not limited to, nickel(II) acetate, nickel(II) acetate tetrahydrate, nickel(II) acetylacetonate, nickel(II) hexafluoroacetylacetonate, nickel (II) octanoate, ammonium nickel(II) sulfate, nickel(II) chloride, nickel(II) bromide, nickel(II) fluoride, nickel(II) iodide, nickel(II) carbonate, nickel(II) hydroxide, nickel(II) nitrate, nickel(II) perchlorate, nickel(II) sulfate, nickel(II) sulfamate, and hydrates thereof, and mixtures thereof. In some embodiments, a nickel salt having a different oxidation state, such as +1, +3, +4, may be used.

Exemplary cobalt salts include, but are not limited to, cobalt(II) nitrate, cobalt(II) nitrate hexahydrate, cobalt(II) chloride, cobalt(II) acetate, cobalt(II) sulfate, cobalt(II) bromide, cobalt(II) iodide, and mixtures and hydrates thereof. In some embodiments, a cobalt salt having a different oxidation state, such as +3 (e.g. cobalt(III) fluoride), +5 (e.g. potassium percobaltate), may be used.

The weight ratio of the salt of the primary catalytic metal to the salt of the promoter may be selected to provide the hydrodesulfurization catalyst with a weight ratio of primary catalytic metal to promoter (e.g., Mo:Co or Mo:Ni) of 1.5:1 to 5:1, preferably 2:1 to 4.5:1, preferably 2.5:1 to 4:1, preferably 3:1 to 3.5:1.

In some embodiments, the aqueous solution optionally also includes a chelating agent. Exemplary chelating agents that may be used during the impregnation step and subsequent mixing operations, include, but are not limited to, ethylenediaminetetraacetic acid (EDTA), citric acid, N-hydroxy ethylenediaminetetraacetic acid, diammonium ethylenediaminetetraacetic acid, as well as oxalic acid, malic acid, sebacic acid, tartaric acid, glucose, amino acids such as glutamine and histidine, other triprotic acids such as isocitric acid, aconitic acid, nitriloacetic acid, and propane-1,2,3-tricarboxylic acid, other tetraprotic acids such as cyclohexanediaminetetraacetic acid, and ethyleneglycol-bis-(beta-aminoethylether)-N,N'-tetraacetic acid, diethylenetriaminepentaacetic acid, urea, thiourea, tris(2-aminoethyl)amine, triethylenetetraamine, tetraethylenepentaamine, and derivatives thereof.

In some embodiments, the aqueous solution optionally also includes an acid. The acid may be an inorganic or organic acid such as hydrochloric acid, formic acid, benzoic acid, acetic acid, phosphoric acid, hydrobromic acid, hydroiodic acid, nitric acid, hydrofluoric acid, sulfuric acid, and/or perchloric acid or some other acid.

After adding the aqueous solution containing the desired salts to the suspension to form a catalyst mixture, the catalyst mixture may be optionally mixed by stirring, shaking, swirling, sonicating, blending, or by otherwise agitating. The catalyst mixture may be optionally heated to 40 to 100° C., preferably 60 to 100° C., preferably 80 to 90° C., or otherwise to the reflux temperature of the catalyst mixture, with continuous mixing for 1 to 10 hours, preferably 2 to 9 hours, preferably 3 to 8 hours, preferably 4 to 7 hours, preferably 5 to 6 hours.

The catalyst mixture may next be filtered to obtain a wet catalyst, and the wet catalyst may be dried at 40 to 100° C., preferably 60 to 100° C., preferably 80 to 90° C. for any amount of time suitable for adequate drying, typically for 1 to 10 hours, preferably 2 to 9 hours, preferably 3 to 8 hours, preferably 4 to 7 hours, preferably 5 to 6 hours. In some embodiments, the wet catalyst is dried in an oven.

After drying, the dried catalyst is preferably calcined thereby producing the hydrodesulfurization catalyst. Calcination may be performed at a temperature of 160 to 500° C., 200 to 450° C., 250 to 400° C., 275 to 375° C., or 300 to 350° C., for example from 1 to 8 hours, preferably 2 to 6 hours, preferably 2.5 to 4 hours, preferably 3 hours. Calcination can be carried out within shaft furnaces, rotary kilns, multiple hearth furnaces, and/or fluidized bed reactors. Calcination may be carried out under oxygen environments including air, in an inert gas (e.g., nitrogen, argon, etc.), or under vacuum, preferably under an inert gas, preferably nitrogen.

Hydrodesulfurization Methods

The present disclosure also provides a method for desulfurizing a hydrocarbon feedstock that includes a sulfur-containing compound. In general, the method involves contacting the hydrocarbon feedstock with the hydrodesulfurization catalyst in the presence of hydrogen ($H_2$) gas, whereby the sulfur-containing compound is desulfurized into a mixture of a desulfurized product and $H_2S$ gas. The $H_2S$ gas can be subsequently removed from the mixture, leaving a desulfurized hydrocarbon stream.

Hydrocarbon Feedstock

Any hydrocarbon feedstock that contains a sulfur-containing compound may be desulfurized in the disclosed methods. The hydrocarbon feedstock may be delivered from a hydrocarbon reservoir or directly from an offshore or an onshore well. For example, the hydrocarbon feedstock may be a crude oil/petroleum or a gaseous stream that is produced from an oil well, particularly from a sour gas oil well.

The hydrocarbon feedstock may also be a distillation product obtained from an oil/petroleum refinery, for example, a fractionized product obtained from the atmospheric distillation unit of an oil/petroleum refinery or the vacuum distillation unit of an oil/petroleum refinery. Thus, in addition to crude oil, the hydrocarbon feedstock may be a naphtha (e.g., light naphtha, heavy naphtha), a kerosene/paraffin, a jet fuel, a fuel oil, a diesel fuel (e.g., a diesel oil, a light diesel oil, a heavy diesel oil), a gas oils (e.g., heavy vacuum gas oil, light vacuum gas oil, light cyclic gas oil), a mineral oil, or any other petroleum distillates, and any combination thereof.

Additionally, the hydrocarbon feedstock may be obtained from any other refinery/upgrading process in an oil/petroleum refinery. For example, the hydrocarbon feedstock may be an effluent obtained from a fluid hydrocarbon cracking unit, for example, a fluid catalytic cracking (FCC) unit that produces FCC naphtha, in which the FCC naphtha may be in need of desulfurization. Therefore, the hydrocarbon feedstock may also be a petrol (gasoline), diesel fuel, FCC naphtha, liquid petroleum gas (LPG), a effluent containing unsaturated olefin compounds, a cracked gas oil, a cycle oil, and a light gas, including mixtures thereof, with specific mention being made to FCC naptha.

The term "naphtha" refers to the middle boiling range hydrocarbon fraction or fractions that are major components of gasoline, while the term "FCC naphtha" refers to a preferred naphtha that has been produced by the well-known process of fluid catalytic cracking. Naphthas having a middle boiling range are those having boiling points from about 10 to about 232° C at atmospheric pressure, preferably from about 21 to about 221° C. Naphtha produced in an FCC process without added hydrogen contains a relatively high concentration of olefins and aromatics. Other naphthas such as steam cracked naphtha and coker naphtha may also contain relatively high concentrations of olefins. Typical olefinic naphthas have olefin contents from about 5 to about 60 wt. %, preferably about 10 to about 40 wt. %; sulfur contents from about 300 ppm to about 7000 ppm; and nitrogen contents from about 5 ppm to about 500 ppm, each based on the weight of the naphtha. Olefins include open chain olefins, cyclic olefins, dienes and cyclic hydrocarbons with olefinic side chains. Because olefins and aromatics are high octane number components, olefinic naphtha generally exhibits higher research and motor octane values than does hydrocracked naphtha. While olefinic naphthas are typically high in olefin content, they may also contain other compounds, especially sulfur-containing and nitrogen-containing compounds, and thus may be particularly suited for desulfurization according to the methods herein.

In preferred embodiments, the hydrocarbon feedstock is selected from the group consisting of light naphtha (obtained from the atmospheric distillation unit), heavy naphtha (obtained from the atmospheric distillation unit), diesel oil (obtained from the atmospheric distillation unit), and FCC naphtha (obtained from the fluid catalytic cracking unit).

In terms of the sulfur-containing compound(s) present in the hydrocarbon feedstock, there is a well-established hierarchy in the ease of sulfur removal from the various organo-sulfur compounds common to refinery and chemical streams. Simple aliphatic, naphthenic, and aromatic mercaptans, sulfides, di- and polysulfides and the like surrender their sulfur more readily than the class of heterocyclic sulfur compounds comprised of thiophene and its higher homologs and analogs. Within the generic thiophenic class, desulfurization reactivity generally decreases with increasing molecular structure and complexity. While simple thiophenes represent the relatively liable sulfur types, the other extreme, which is sometimes referred to as 'hard sulfur' or 'refractory sulfur', is represented by the derivatives of dibenzothiophene, especially those mono- and di-substituted and condensed ring dibenzothiophenes bearing substituents on the carbons beta to the sulfur atom. These highly refractory sulfur heterocycles resist desulfurization as a consequence of steric inhibition precluding the requisite catalyst-substrate interaction. For this reason, these sulfur-containing compounds commonly survive traditional desulfurization processes and they poison subsequent processes whose operability is dependent upon a sulfur sensitive catalyst(s). Destruction of these 'hard sulfur' containing compounds can be accomplished under relatively severe process conditions, but this may prove to be economically undesirable owing to the onset of harmful side reactions leading to feed and/or product degradation. Also, the level of investment and operating costs required to drive the severe process conditions may be too great for the required sulfur specification. Therefore, hydrodesulfurization catalysts that can remove such 'hard' sulfur-containing compounds under relatively mild conditions are desirable.

Exemplary sulfur-containing compounds which can be degraded by the methods herein include, but are not limited to, elemental sulfur, carbon disulfide, dimethyl disulfide, ethyl disulfide, propyl disulfide, isopropyl disulfide, butyl disulfide, tertiary butyl disulfide, thianaphthene, thiophene, secondary dibutyl disulfide, thiols, methyl mercaptan, phenyl mercaptan, cyclohexγthiol, methyl sulfide, ethyl sulfide, propyl sulfide, isopropyl sulfide, butyl sulfide, secondary dibutyl sulfide, tertiary butyl sulfide, thiocyclohexane, benzothiophene, alkyl benzothiophene, dibenzothiophene, alkyl dibenzothiophene, dialkyl dibenzothiophene, and any combination thereof.

In some embodiments, the sulfur-containing compound is at least one selected from the group consisting of a sulfide, a disulfide, a thiophene, a benzothiophene, and a dibenzothiophene. In preferred embodiments, the sulfur-containing compound is a dibenzothiophene. Exemplary dibenzothiophene compounds include, but are not limited to, dibenzothiophene (DBT), 3-methylbenzothiophene, 4-methyldibenzothiophene, 4,6-dimethyldibenzothiophene, and 4,6-diethyldibenzothiophene. In preferred embodiments, the sulfur-containing compound is dibenzothiophene, 4,6-dimethyldibenzothiophene, or both.

The concentration of the sulfur-containing compound in the hydrocarbon feedstock may vary depending on the particular hydrocarbon feedstock to be desulfurized, the source of the crude oil, and any refining steps the hydrocarbon feedstock has been subject to. In some embodiments, the sulfur-containing compound may be present in the hydrocarbon feedstock at a concentration of 100 to 7,000 ppm, preferably 150 to 6,000 ppm, preferably 200 to 5,000 ppm, preferably 250 to 4,000 ppm, preferably 300 to 3,000 ppm, preferably 350 to 2,000 ppm, preferably 400 to 1,000 ppm, preferably 450 to 900 ppm, preferably 500 to 850 ppm, preferably 550 to 800 ppm, preferably 600 to 750 ppm, preferably 650 to 700 ppm.

In addition to containing the sulfur-containing compound, the hydrocarbon feedstock may also include hydrogen, $CO_2$, and various hydrocarbon compounds, depending on the origin of the hydrocarbon feedstock, such as $C_{1-30}$ hydrocarbon compounds, preferably $C_{2-25}$ hydrocarbon compounds, preferably $C_{3-20}$ hydrocarbon compounds, preferably $C_{4-15}$ hydrocarbon compounds. Examples of hydrocarbon compounds which may be present in the hydrocarbon feedstock include, but are not limited to, $C_{1-20}$ normal paraffins (e.g., methane, ethane, propane, butane, and higher alkanes such as octane), $C_{4-20}$ isoparaffins (e.g., isobutene, isopentane, neopentane), $C_{3-20}$ cycloparaffins or naphthenes (e.g., cyclopropane, cyclopentane, cyclohexane, norbornene, decalin, bicyclohexyl), $C_{6-20}$ aromatics (e.g., benzene, toluene, xylenes, ethylbenzene, methylethylbenzene, diethylbenzene, isomers of trimethylbenzene, dimethylethylbenzene, isomers of tetramethylbenzene, cumene, pseudocumene, propyl-substituted benzenes, butyl-substituted benzenes, biphenyl, cyclohexyl benzene) and in the event the hydrocarbon feedstock contains olefins, for example if the hydrocarbon feedstock is FCC naphtha, then $C_{2-20}$ olefins (e.g., ethene, propene, butenes, isobutene, 1,3-butadiene, pentenes, isopentenes, cyclopentadiene, dicyclopentadiene, and higher olefins) may also be present. Additionally, the hydrocarbon feedstock may also include nitrogen compounds such as pyridines, piperidines, quinolones, and porphyrins.

Contacting

The hydrocarbon feedstock may be contacted with the hydrodesulfurization catalyst in the presence of $H_2$ gas under favorable reaction conditions to convert at least a portion of the sulfur-containing compound into a mixture of $H_2S$ and a desulfurized product.

In some embodiments, the hydrocarbon feedstock is contacted with the hydrodesulfurization catalyst at a temperature of 150 to 500° C., preferably 200 to 450° C., preferably 250 to 400° C., preferably 300 to 350° C. The hydrodesulfurization reaction may be conducted for 0.1 to 10 hours, 0.5 to 9 hours, 1 to 8 hours, 2 to 7 hours, or 3 to 6 hours.

The hydrocarbon feedstock may be contacted with the hydrodesulfurization catalyst using various pressures of $H_2$ gas, typically under $H_2$ pressures of 30 to 80 bars, preferably 35 to 75 bars, preferably 40 to 70 bars, preferably 45 to 65 bars, preferably 50 to 60 bars, preferably 55 bars. A volumetric flow ratio of the $H_2$ gas to the hydrocarbon feedstock may vary depending on the type of sulfur-containing compound present in the hydrocarbon feedstock, however, typical volumetric flow ratios of the $H_2$ gas to the hydrocarbon feedstock range from 100:1 to 1:100, preferably 80:1 to 1:80, preferably 50:1 to 1:50, preferably 40:1 to 1:40, preferably 30:1 to 1:30, preferably 20:1 to 1:20, preferably 15:1 to 1:15, preferably 10:1 to 1:10, preferably 5:1 to 1:5, preferably 3:1 to 1:3, preferably 2:1 to 1:2, preferably 1:1.

The hydrocarbon feedstock may be contacted with the hydrodesulfurization catalyst using any technique known to those of ordinary skill in the art, depending on the physical state of the hydrocarbon feedstock. For example, depending on the type of process stream, the hydrocarbon feedstock may be in a liquid state or a gaseous state based on the boiling point of its components. In some embodiments, the hydrocarbon feedstock is in a liquid state or in a gaseous state and the hydrocarbon feedstock is passed through a catalyst bed of the hydrodesulfurization catalyst contained within a reactor such as a fixed-bed reactor or a fluidized-bed reactor. In preferred embodiments, the hydrodesulfurization catalyst is contained within a fixed-bed reactor, and the hydrocarbon feedstock is passed through the fixed-bed reactor to convert the sulfur containing compound into a mixture of $H_2S$ and a desulfurized product. In the petroleum refining industry, the reactor (e.g., fixed-bed reactor) may be a component of an hydrodesulfurization (HDS) unit, commonly referred to as a hydrotreater. In some embodiments, the hydrocarbon feedstock is in a gaseous state and the hydrocarbon feedstock is passed over the hydrodesulfurization catalyst, or may stay stagnant over the hydrodesulfurization catalyst, i.e., as an atmosphere to the catalyst for desulfurization. In some embodiments, the hydrocarbon feedstock is in a liquid state and the hydrocarbon feedstock is mixed with the hydrodesulfurization catalyst to form a heterogeneous mixture in a batch reactor equipped with a rotary agitator.

In some embodiments, the hydrodesulfurization catalyst is present in a catalyst chamber within a reactor, and the contacting includes feeding the hydrocarbon feedstock into the catalyst chamber of the reactor with a weight hourly space velocity (WHSV) of 0.5 to 10 $h^{-1}$, preferably 1 to 9 $h^{-1}$, preferably 2 to 8 $h^{-1}$, preferably 3 to 7 $h^{-1}$, preferably 4 to 6 $h^{-1}$, preferably 5 $h^{-1}$. In some embodiments, the hydrocarbon feedstock has a residence time in the reactor/catalyst chamber of less than 1 hour, preferably less than 40 minutes, preferably less than 30 minutes, preferably less than 20 minutes, preferably less than 15 minutes, preferably less than 10 minutes, preferably less than 5 minutes. The shortest residence time the hydrocarbon feedstock is present in the reactor will be the time taken for the hydrocarbon feedstock to be transported from the inlet of the reactor to the outlet of the reactor.

The loading of the catalyst may vary significantly depending on the type of sulfur-containing compound, the hydrocarbon feedstock, and the concentration of the sulfur-containing compound in the hydrocarbon feedstock. Generally, the hydrodesulfurization catalyst is employed in an amount of 0.1 to 5 g per 100 mL of the hydrocarbon feedstock, preferably 0.2 to 4.0 g per 100 mL, preferably 0.3 to 3.0 g per 100 mL, preferably 0.4 to 2.0 g per 100 mL, preferably 0.5 to 1.5 g per 100 mL, preferably 0.6 to 1.0 g per 100 mL of the hydrocarbon feedstock.

In some embodiments, the contacting converts 40 to 99%, preferably 50 to 98%, preferably 60 to 96%, preferably 70 to 94%, preferably 80 to 92%, preferably 85 to 90%, by weight of the sulfur-containing compound present in the hydrocarbon feedstock into a mixture of $H_2S$ and a desulfurized product.

The desulfurized product may be directly analogous to the sulfur-containing compound except that any sulfur carbon bond present in the sulfur-containing compound is preferably replaced with a carbon hydrogen bond in the desulfurized product. For example, when the sulfur-containing compound is dibenzothiophene, the desulfurized product may include biphenyl. The desulfurized product may also include any hydrogenation products derivable from the directly analogous desulfurized product where C—S bonds have been replaced with C—H bonds. That is, in the example provided above where dibenzothiophene is desulfurized into biphenyl, the biphenyl may be at least partially or completely hydrogenated to form one or more of cyclohexyl benzene and bicyclohexyl. The desulfurized product thus may be a mixture of one or more of biphenyl, cyclohexyl benzene, and bicyclohexyl when dibenzothiophene is present in the hydrocarbon feedstock. The sulfur-containing byproduct of such a desulfurization reaction is in most cases $H_2S$.

Of course, in addition to the desulfurized product, the $H_2S$, and the excess H2 gas employed during the contacting, the mixture formed from the contacting may also include any $CO_2$, nitrogen containing compounds, and/or other various hydrocarbon compounds present in the hydrocarbon feedstock as described above.

Removing

The method disclosed herein may also include removing the $H_2S$ from the mixture to form a desulfurized hydrocarbon stream. Removing the $H_2S$ from the mixture may be accomplished using any technique known to those of ordinary skill in the art, and specifically includes distillation, absorption, adsorption, solvent extraction, stripping, and filtration. For example, the $H_2S$ may be removed using a gas separator, a sour water stripper, a sour water steam stripper, and/or an amine gas treating unit as is known in the art. The removed $H_2S$ may be collected and further supplied to a sulfur manufacturing plant to produce sulfur-containing products such as elemental sulfur (e.g., in a Claus sulfur plant) and/or sulfuric acid in a wet sulfuric acid process or in the conventional contact process.

In some embodiments, a sulfur content of the desulfurized hydrocarbon stream is less than 100 ppm, preferably less than 75 ppm, preferably less than 50 ppm, preferably less than 40 ppm, preferably less than 30 ppm, preferably less than 20 ppm, preferably less than 15 ppm, preferably less than 10 ppm, preferably less than 5 ppm.

One non-limiting example for the desulfurization method will now be described. It should be understood that the following description is not meant to be limiting, and various other process flows, procedures, parameters, variations, and equipment are also contemplated. The hydrocarbon feedstock may be pumped up to an elevated pressure, if desired, where it is joined by a stream of $H_2$ gas, for example hydrogen-rich recycle gas. The resulting feed mixture may be optionally preheated by flowing through a heat exchanger and then flowed through a fired heater where the feed mixture is totally vaporized and heated before entering a reactor housing a fixed-bed of the hydrodesulfurization catalyst, where the hydrodesulfurization reaction takes place. The resulting hot reaction products may be optionally partially cooled by flowing through the heat exchanger where the reactor feed mixture was preheated, and then may be flowed through a water-cooled heat exchanger prior to being routed through a pressure controller (PC) where it may undergo a pressure reduction down to about 3 to 10 atmospheres, or about 4 to 6 atmospheres, or about 5 atmospheres. The depressurized mixture of liquid and/or gaseous reaction products may then be delivered to a gas separator vessel at about 30 to 50° C., preferably 35° C. Most of the hydrogen-rich gas from the gas separator vessel is recycle gas, which may be routed through an amine contactor for removal of the reaction product $H_2S$ that it contains. The $H_2S$-free hydrogen-rich gas may then recycled back for reuse in the reactor for the hydrodesulfurization reaction. Any excess gas from the gas separator vessel may be combined with the sour gas from the stripper as described below. The liquid from the gas separator vessel may be flowed through a reboiled stripper distillation tower (stripper). The bottoms product from the stripper is the desulfurized hydrocarbon stream. The overhead sour gas from the stripper may contain hydrogen, hydrogen sulfide ($H_2S$), and may also optionally contain any other high boiling components from the hydrocarbon stream such as methane, ethane, propane, and perhaps in some cases butane and heavier hydrocarbon compounds. In the cases where the hydrocarbon feedstock contains olefins, for example when the hydrocarbon feedstock is a naphtha derived from a refinery fluid catalytic cracker (FCC) unit, then the overhead sour gas from the stripper may also contain some ethene, propene, butenes, pentenes, or heavier olefinic components. That sour gas is preferably sent to the refinery's central gas processing plant for removal of the hydrogen sulfide in the refinery's main amine gas treating unit and through a series of distillation towers for recovery of any propane, butane, pentane or heavier components, and when olefinic components are present, for recovery of those olefinic components. Any residual hydrogen, methane, ethane, and some propane may be used as refinery fuel gas. The hydrogen sulfide removed and recovered by the amine gas treating unit may be subsequently converted to elemental sulfur in a Claus process unit or to sulfuric acid in a wet sulfuric acid process or in a contact process.

The desulfurized hydrocarbon stream recovered from the methods of the present disclosure may be, or may be used to generate, an ultra-low-sulfur fuel oil, an ultra-low-sulfur diesel, an ultra-low-sulfur gasoline, or an ultra-low-sulfur heating oil, which meet environmental regulations such as the US Environmental Protection Agency (EPS) standards for sulfur content for use as fuels in automotive vehicles, aircraft, railroad locomotives, ships, gas or oil burning power plants, residential and industrial furnaces, and other forms of fuel combustion. The combustion of such desulfurized hydrocarbon streams advantageously provide reduced sulfur dioxide ($SO_2$) emissions, compared to hydrocarbons which have not been desulfurized.

The desulfurized hydrocarbon streams produced by the methods herein may also be delivered to other refinement/upgrading process units in an oil/petroleum refinery, including, but not limited to, a catalytic reforming unit, an isomerization plant, and an alkylating unit. For example, the desulfurized hydrocarbon stream may be a desulfurized naphtha stream which is sent to a catalytic reforming unit used to upgrade the octane rating of the desulfurized naptha stream. Here, the catalytic reformer typically contains a noble metal catalyst which is used to convert the desulfurized naphtha molecules into higher-octane molecules to produce reformate (reformer product), which is eventually incorporated as a component of the end-product gasoline or petrol. Sulfur is advantageously removed from the feed streams of such refinement/upgrading process units within a petroleum refinery because sulfur, even in extremely low concentrations, can poison the catalysts (e.g., noble metal catalysts such as platinum and rhenium) in such refinement/upgrading process units.

The examples below are intended to further illustrate protocols for preparing and using the hydrodesulfurization catalysts in desulfurization methods, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Experimental Section
Chemicals

Commercial zeolite Y type, polyvinylpyrrolidone $(C_6H_9NO)_n$, decalin (purity 99%), dibenzothiophene (DBT) (purity 98%), ammonium molybdate tetrahydrate (purity 98%), cobalt nitrate hexahydrate (purity 98%), nickel acetate tetrahydrate (purity 98%), and ethanol (purity 99%) were purchased from Sigma Aldrich.

Preparation of the Catalyst

The composite support of zeolite-graphene (ZG) was obtained by mixing graphene oxide dispersed in water and commercial zeolite (Y type). A sol-gel method was used to mix around 20 mg of graphene oxide dispersed in water with 6.4 g of zeolite. During this process, 100 ml of deionized water, 0.2 gm of polyvinylpyrrolidone (to enhance the interaction between the two supports beside its role for dispersing the active phase), and 10 ml ethanol were added to ZG. Stirring of the composite support was for 1 h and refluxing 5 h at 110° C. After cooling, the filtration was performed to separate the filtrate which was then dried at 90° C.

The incipient wetness impregnation method was used for adding the active phases molybdenum (Mo) and cobalt (Co) or nickel (Ni) nanoparticles to the support with a ratio of 15% Mo and 5% Co (Ni) respectively. Selection of these percentages for the active phases was decided after literature survey and found that Co (Ni) from 1-5% and Mo catalyst from 8-15%. See Q. Zhang, W. Qian, S. Oshima, A. Ishihara, T. Kabe, the role of cobalt on hydrodesulfurization and hydrogenation of dibenzothiophene and 4,6-dimethyldibenzothiophene catalyzed by Co-Mo/Al$_2$O$_3$ Sekiyu Gakkaishi (Journal Japan Pet. Institute). 40 (1997), incorporated herein by reference in its entirety. A solution of cobalt nitrate (1.97 gm) and ammonium molybdate (2.43 gm) was prepared. Also, around 5.53 gm of ZG support dispersed in 100 ml deionized water kept under stirring at 90° C. for 30 min. The solution was mixed with the ZG support dispersion under stirring at 100° C. for 5 h. The catalyst as a final product was filtered and dried at 100° C. for 5 h. Catalyst calcination in pure nitrogen medium was performed at 350° C. for 3 h. The catalyst made of MoCo supported on the graphene doped zeolite is referred to as "ZGMC". The catalyst made of MoNi catalyst supported on the graphene doped zeolite is referred to as "ZGMI". When synthesizing the reference catalysts ZMC (MoCo on non-doped zeolite support) or ZMI (MoNi on non-doped zeolite support), the same steps were used but without incorporation of graphene for comparison.

Many techniques have been used to illustrate the catalysts properties such as BET N$_2$ physisorption, powder x-ray diffraction (XRD), fourier transform infrared (FT-IR), scanning electron microscope (SEM), electron dispersive spectroscopy (EDS), and thermogravimetric analysis (TGA).

Assessment of the Catalysts

A batch reactor (model 4848B) from Parr instruments co. was used to evaluate the activity of the catalysts (ZGMI, ZGMC, ZMC and ZMI) for hydrodesulfurization of dibenzothiophene. Decalin acted as a solvent model fuel for dissolving DBT to make hydrocarbon feedstock solution for HDS of DBT with 0.5% of sulfur. The catalytic reaction conditions were 55 bars for hydrogen partial pressure and 300° C. as reaction temperature. About 0.6 gm of the synthesized catalysts were interacted with 100 ml of decalin containing DBT. The initial concentration of DBT was 550 S-ppm. The reaction was started when inserting the mixture into the vessel of the reactor. Collection of six sample and zero point (first sample) was taken after the temperature of the reaction come to 300° C. Reaction monitoring during 5 h was mandatory with collecting sample every hour by manual valve. Determination of the sulfur concentration for the collected samples was carried out by gas-chromatography sulfur chemiluminescence detector (GC-SCD). Finally, GC-MS was used to identify the samples.

Results and Discussion
Physico-Chemical Properties

The N$_2$ adsorption-desorption isotherms and pore size distribution of the four catalysts (ZGMI, ZGMC, ZMC and ZMI) are shown in FIGS. 1A-1H. Also, the textural properties of the catalysts are illustrated in Table 1. Incorporation of graphene within the zeolite to form composite support increased the surface area from 258.4 m$^2$·g$^{-1}$ for ZMC to 302.3 m$^2$·g$^{-1}$ for ZGMC and 285.8 m$^2$·g$^{-1}$ for ZMI to 310.5 m$^2$·g$^{-1}$ for ZGMI. This improvement in surface area has a role to enhance the activity of the catalysts. The isotherm curves are like type IV. At high values of relative pressure, there is a hysteresis loop which clarifies the mesoporous nature of the material while the nitrogen uptake at low pressure indicated the microporous existence within the catalysts. From FIGS. 1B, 1D, 1F, and 1H, the average pore size of the catalysts was from 3.3 nm to 3.8 nm. Therefore, graphene improved the textural properties of the catalysts that lead to an enhanced activity towards hydrodesulfurization of thiophenes. Hierarchy factor (HF) was also calculated to illustrate the graphene role on the textural properties of the catalysts. It was calculated by the following equation (1):

$$HF = \frac{V_{micro}}{V_{total}} \times \frac{S_{meso}}{S_{BET}} \quad (1)$$

By replacing these parameters in eq. (1), the HF was obtained, see Table 1. The HF value for ZGMC and ZGMI are higher than the reference sample ZMC and ZMI which clarifies their higher adsorption efficiency. See J. Peréz-Ramírez, D. Verboekend, A. Bonilla, S. Abelló, Zeolite catalysts with tunable hierarchy factor by pore-growth moderators, Adv. Funct. Mater. 19 (2009) 3972-3979, incorporated herein by reference in its entirety. As per FIGS. 1A, 1C, 1E, and 1G, the quantity adsorbed—desorbed for the inventive catalysts (ZGMI ZGMC) were always higher than the reference catalysts (ZMC and ZMI) at any relative pressure value, which supports the regarding HF.

TABLE 1

Textural properties of the prepared catalysts

| Items | ZMC | ZMI | ZGMC | ZGMI |
|---|---|---|---|---|
| Specific surface area ($m^2 \cdot g^{-1}$) | 258.4 | 285.8 | 302.3 | 310.5 |
| Average pore size (nm) | 3.5 | 3.8 | 3.3 | 3.6 |
| Total Pore volume ($m^3 \cdot g^{-1}$) | 0.22 | 0.24 | 0.27 | 0.28 |
| Hierarchy factor (HF) | 0.016 | 0.019 | 0.025 | 0.027 |

Figure 2:
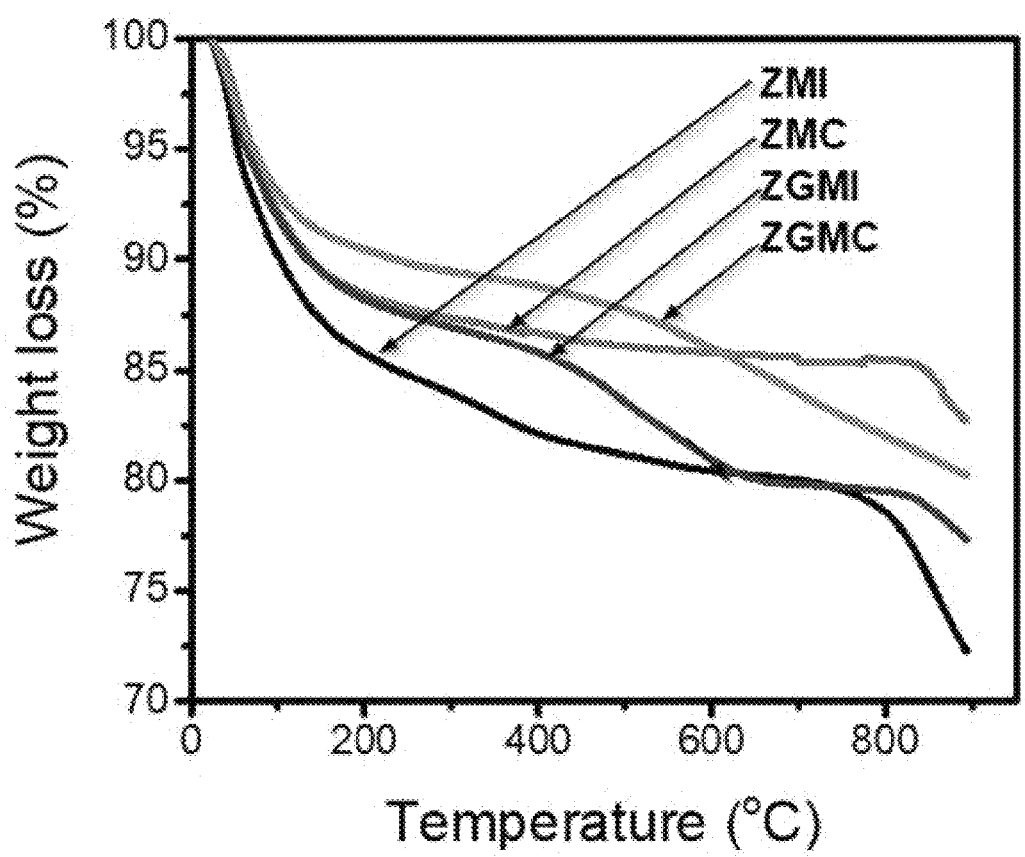
FIG. 2 is a graph illustrating the TGA curves for the four catalysts described herein.
Figure 3A:
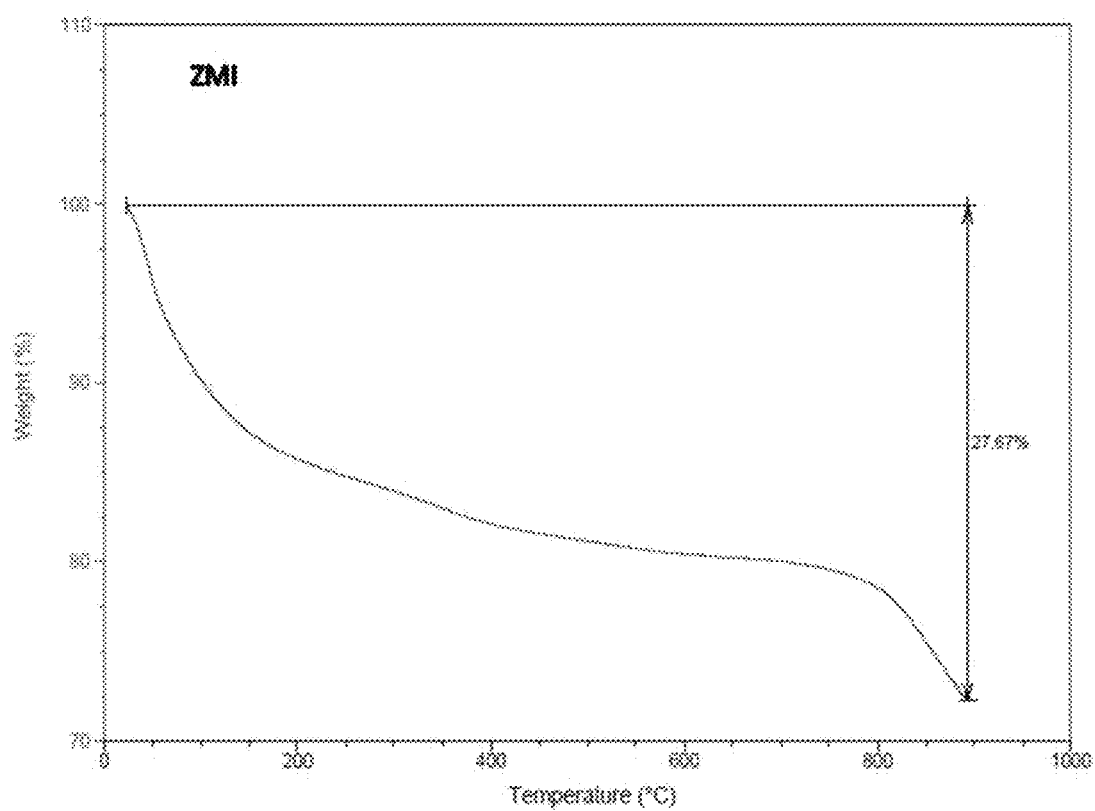
FIGS. 3A-3D are graphs illustrating the TGA plots indicating the exact weight loss % for ZMI (3A), ZMC (3B), ZGMI (3C), and ZGMC (3D)
Figure 3B:
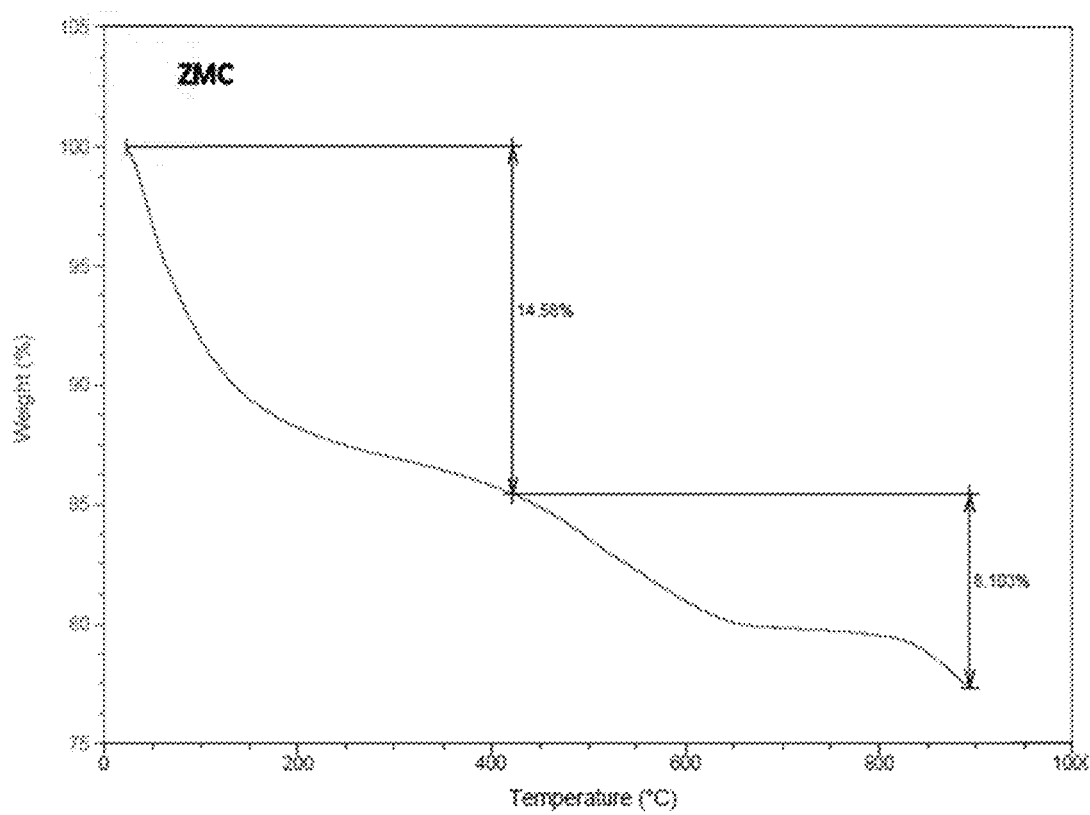
Figure 3C:
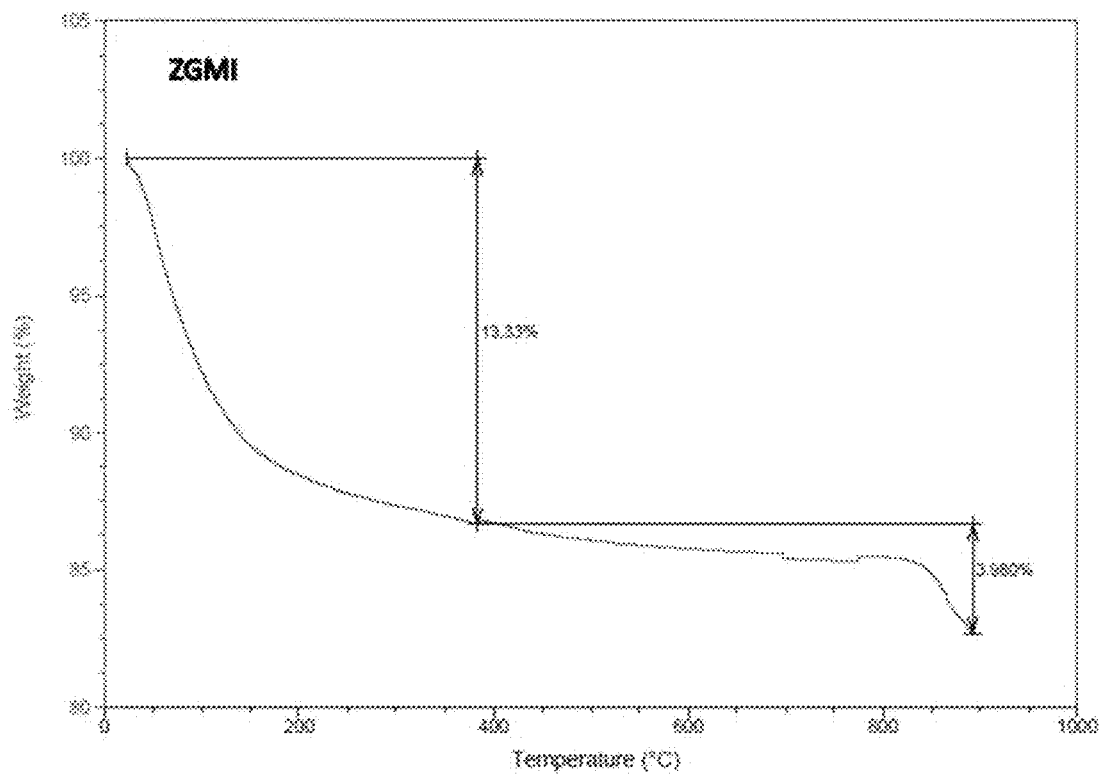
Figure 3D:
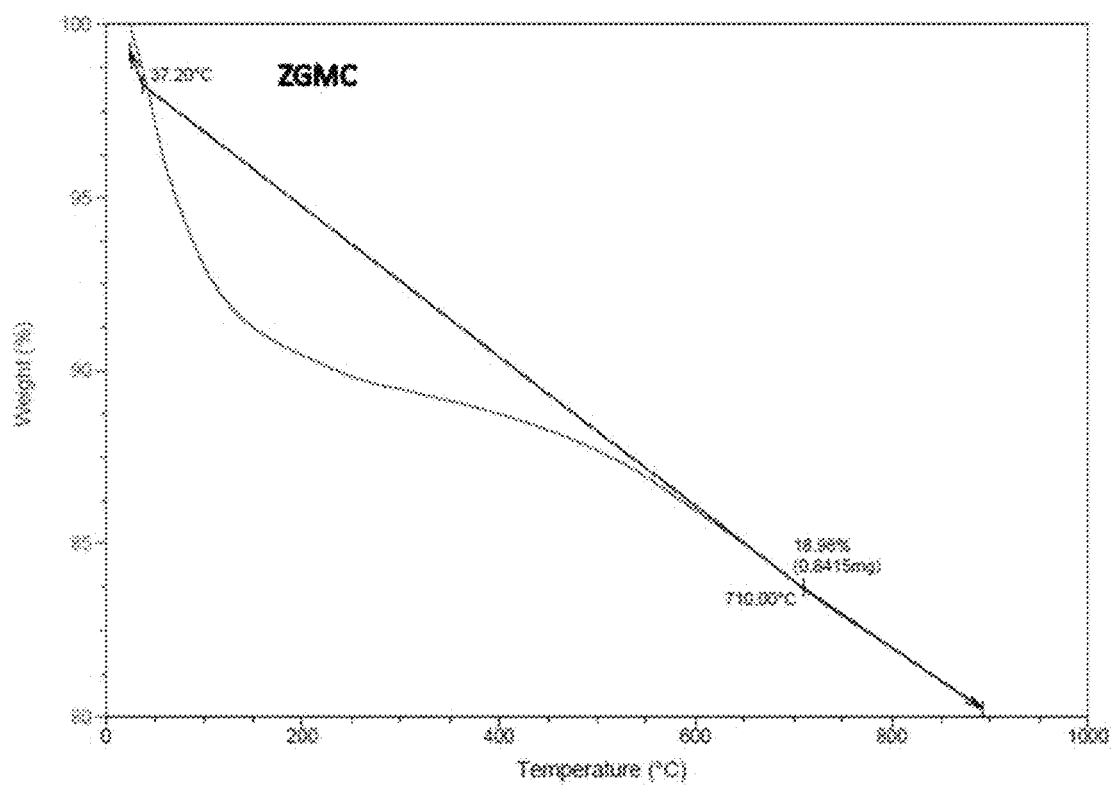

TGA curves were used to investigate the thermal stability and illustrate the effect of HDS reaction temperature on the synthesized catalysts (FIG. 2). The impregnation of graphene into the catalyst component has a crucial effect regarding its stability. As shown in FIGS. 3A and 3C, the weight loss for ZMI reference sample was 17% at 400° C. and 27% at 900° C., while for ZGMI, the weight loss was 13% at 400° C. and reduced only 4% up to 900° C. Also, the weight loss for ZMC was 14.6% at 400° C. and 23% up to 900° C., compared to ZGMC that was 11% and 18% at the same temperature scale (FIGS. 3B and 3D). The total decomposition rate of ZGMC and ZGMI after 900° C. were 18.9% and 17% respectively that was better than the reference ones (ZMC and ZMI) 22.5% and 27% respectively. These results reflect the enhanced thermal stability of the synthesized catalyst after graphene incorporation into zeolite.

Figure 4A:
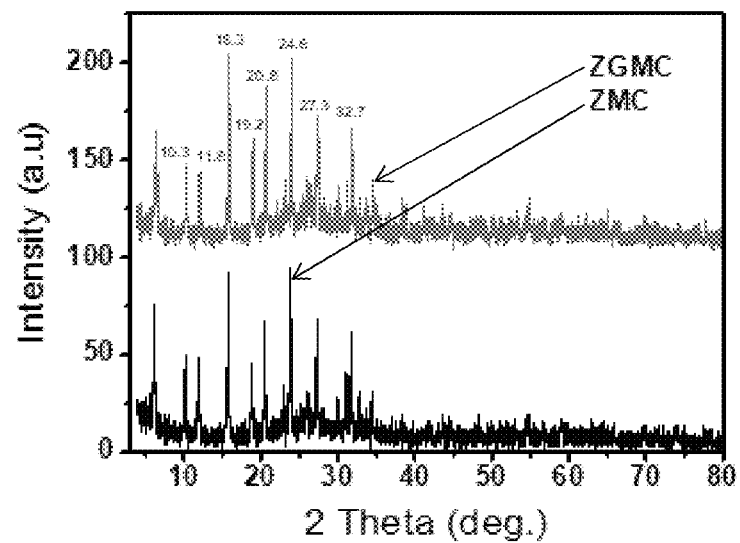
FIGS. 4A-4B are graphs illustrating the XRD pattern for ZGMC and ZMC (4A), ZGMI and ZMI (4B)
Figure 4B:
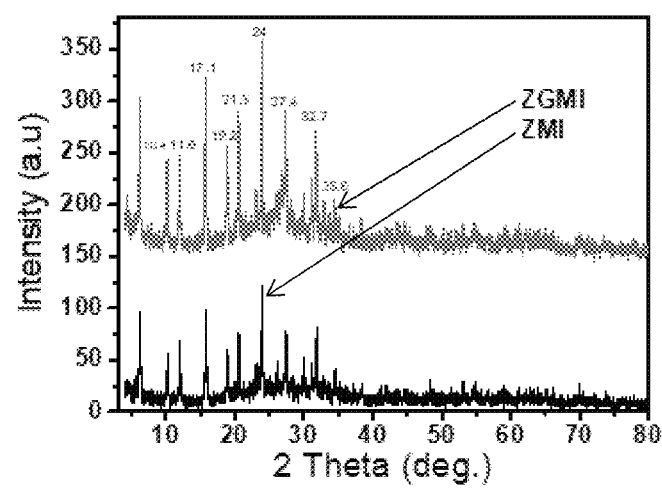
Figure 5A:
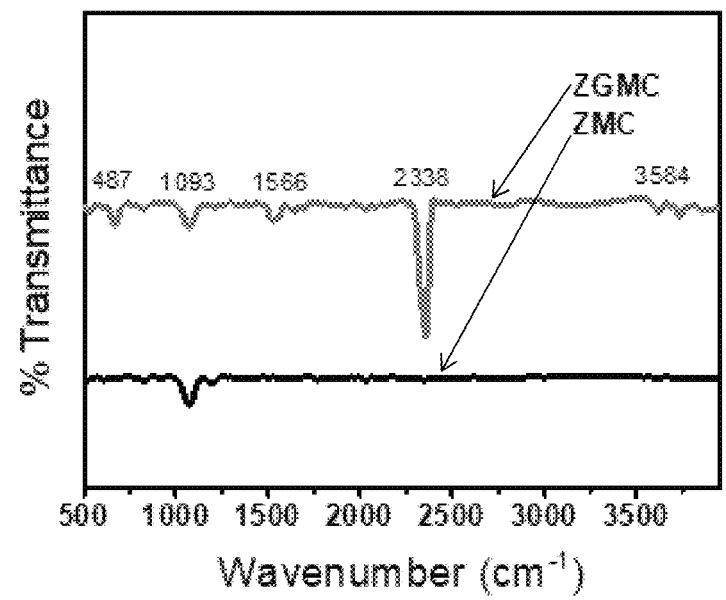
FIGS. 5A-5B are graphs illustrating the spectrum of FTIR for ZGMC and ZMC (5A), ZGMI and ZMI (5B)
Figure 5B:
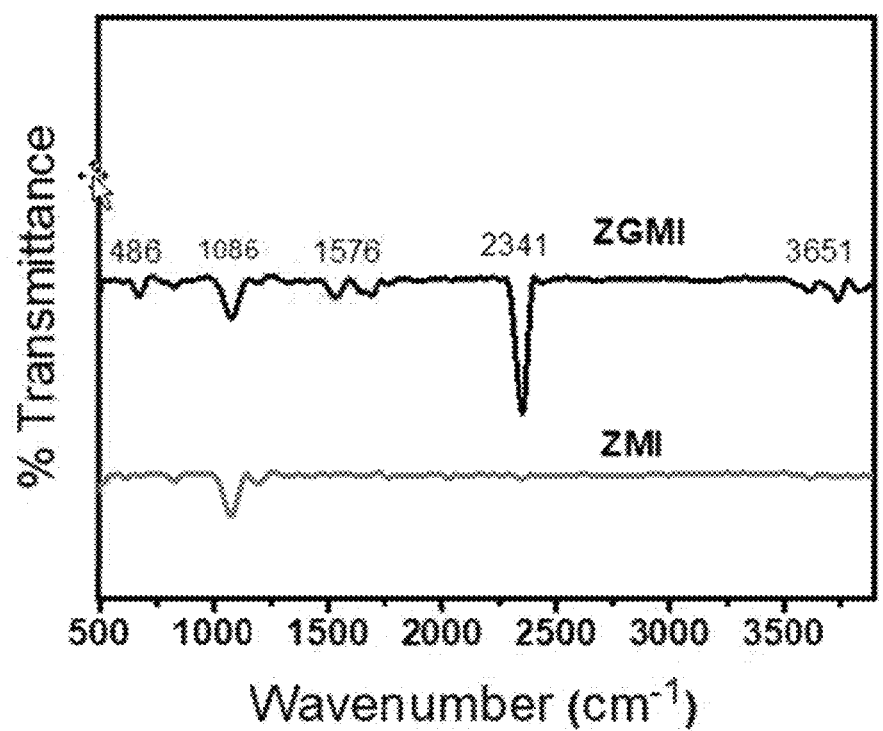

The XRD pattern for the synthesized catalysts are illustrated in FIGS. 4A and 4B, comparing between (ZGMC with ZMC—FIG. 4A) and (ZGMI with ZMI—FIG. 4B). The characteristic peak at 2θ=27.3° was attributed to Co(Ni)MoO$_4$. Other peaks at 2θ=16.3°, 19.2°, 20.8°, 24.6°, 32.7°, 35.6° belong to the zeolite material in the four catalysts. No peaks appeared for the active phases Mo and Co (Ni) due to their enhanced dispersion on the composite support surface which is consistent with nitrogen adsorption-desorption results. In the modified catalyst, there was no diffraction peak for graphene, which may be related to the low diffraction intensity of graphene and its low amount. See Y. Wang, Y. Li, L. Tang, J. Lu, J. Li, Application of graphene-modified electrode for selective detection of dopamine, Electrochem. Commun. 11 (2009) 889-892, incorporated herein by reference in its entirety. In FTIR pattern, the functional groups of the prepared catalysts were investigated. As shown in FIGS. 5A and 5B, a characteristic peak at 3581 cm$^{-1}$ was attributed to OH group stretching mode of graphene oxide. The observed peaks at 486 and 1086 cm$^{-1}$ were related to the Mo=O central vibrational mode. Bands in the range from 450-1000 cm$^{-1}$ indicated the good dispersion of the active phases on the composite support surface. The band at 1566 cm$^{-1}$ may be for OH bending mode.

The catalysts surface morphology and their elemental compositions were evaluated by scanning electron microscope (SEM) and energy dispersive x-ray spectroscopy (EDX). FIGS. 6A-6H illustrated the SEM images for the four catalysts. The surface modification by graphene doping enhanced the dispersion of the active phases Mo and Co (Ni) on the composite support surface. Figures for ZGMC and ZGMI (FIGS. 6E-6H) showed the better distribution of the catalyst and promoter on the catalyst support surface and the role of graphene sheets for enhancing the surface area. From these figures, it was clear graphene sheets are present beside the zeolite support. On the other hand, it was clear in the ZMI and ZMC catalyst (reference samples) images (FIGS. 6A-6D), the dispersion of the active phase Mo and Co (Ni) is poor and not homogenous.

In FIGS. 7A-7D, EDX was used to confirm the presence of elements introduced into the four catalysts compositions (ZMI, ZMC, ZGMI, and ZGMC). All elements Al, Si, Co, Mo and nickel were confirmed their existence in the reference samples (ZMI and ZMC) as per FIGS. 7A and 7B, while carbon element attributed to the graphene incorporation was present in FIGS. 7C and 7D (ZGMI and ZGMC). The zeolite and catalytic metals were successfully introduced into all four catalysts.

In FIGS. 8A-8F, mapping was used to illustrate the distribution and the introduction of all catalyst components. It was shown that all components have been introduced within catalyst with homogenous dispersion without any appearance for agglomeration (see especially Mo and Ni homogeneous dispersion in FIGS. 8E and 8F).

Synthesized Catalysts Activity towards HDS

Figure 9:
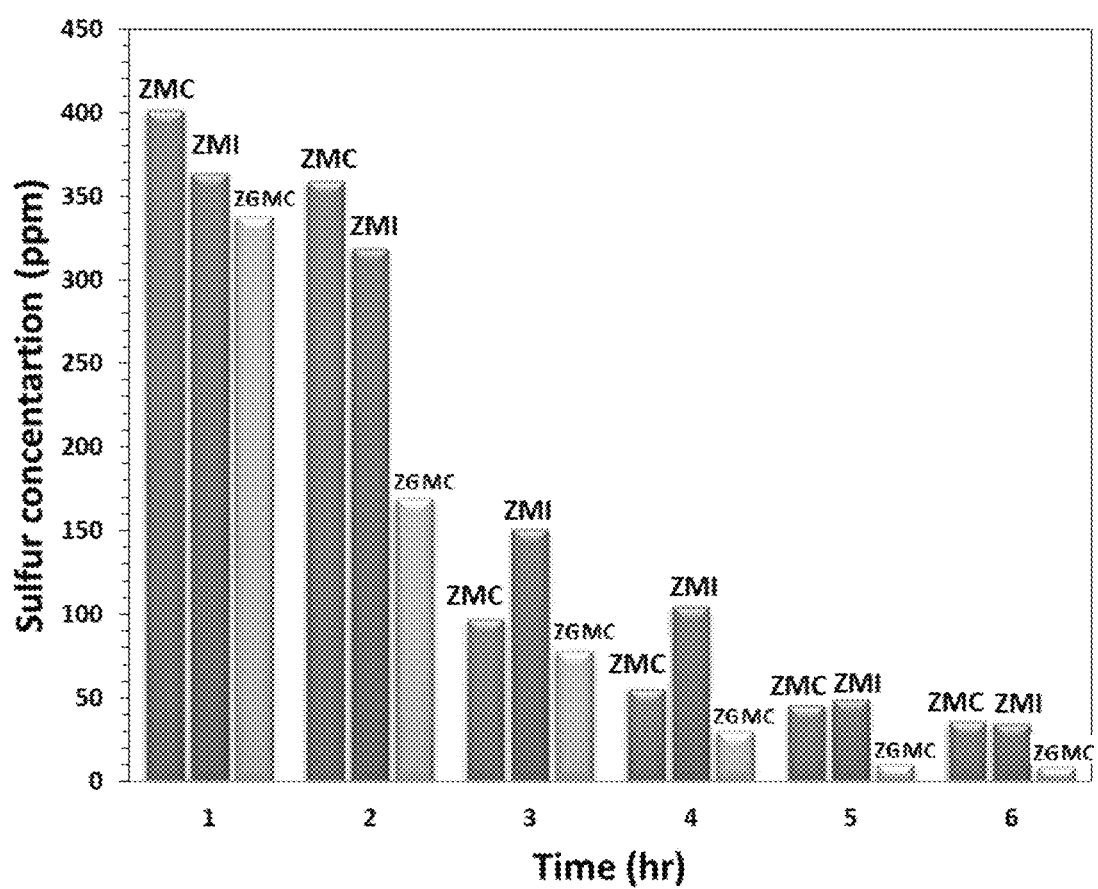
FIG. 9 is a graph illustrating the catalytic activity of catalysts ZMC, ZMI and ZGMC in terms of the sulfur concentration (ppm) in the hydrocarbon feedstock as a function of time (hr)
Figure 10:
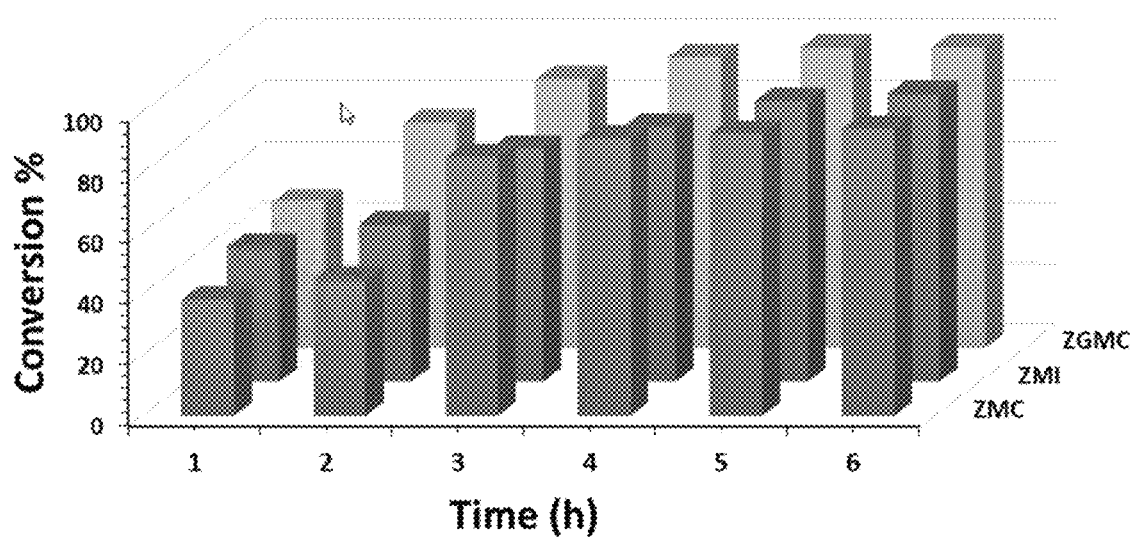
FIG. 10 is a graph illustrating the percentage of conversion of the sulfur-containing compound using ZMC, ZMI and ZGMC catalysts as a function of time (hr)

FIG. 9 illustrates the sulfur concentration of the hydrocarbon feedstock in ppm over the course of a 6 h reaction time for ZMC, ZMI and ZGMC. The reaction parameters used for DBT desulfurization were 300° C. temperature, hydrogen partial pressure of 55 bar, rotation of 190 rpm, catalyst amount (0.6 g), and 100 ml of model fuel (hydrocarbon feedstock). It was observed that after 6 h, the sulfur concentration for reference samples ZMC and ZMI were 35.7 and 34.5 ppm respectively, while for ZGMC was 8.1 ppm of sulfur. The conversion percentage of DBT for the ZMC, ZMI and ZGMC catalysts is illustrated in FIG. 10. It was 94.5%, 94.7% and 98.7% for ZMC, ZMI and ZGMC respectively. The improvement in the surface area of the catalyst after incorporation of graphene has a crucial role in increasing the catalytic activity of ZGMC compared to ZMC and ZMI. Also, HF calculation and adsorption-desorption isotherms support the conclusion regarding the activity of ZGMC. All textural properties like pore volume, surface area and average pore diameter were enhanced with graphene doping that led to the better distribution of the active phases on the composite support surface.

Expected Reaction Mechanism for Hydrodesulfurization

Figure 11:
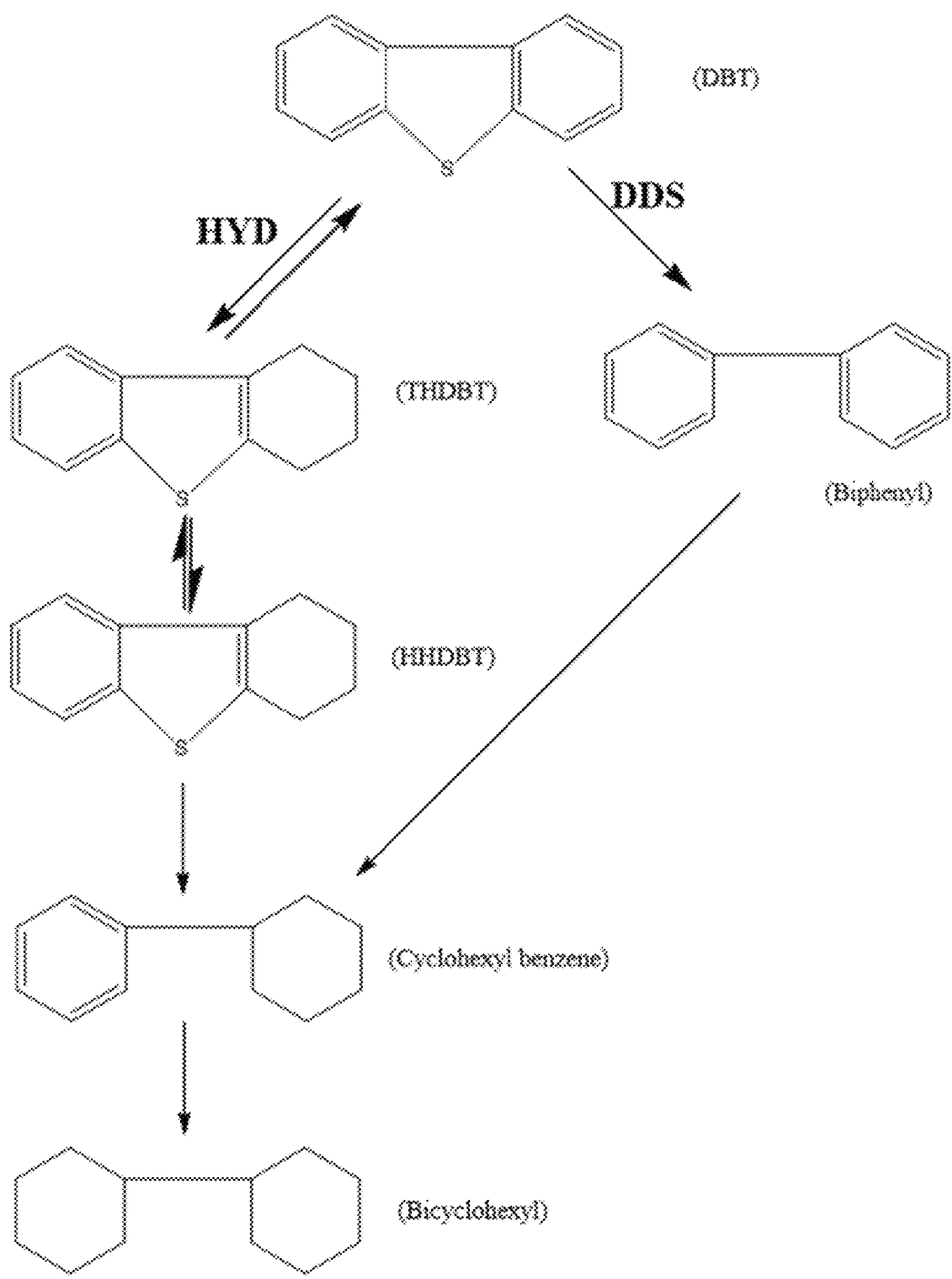
FIG. 11 illustrates the proposed DBT hydrodesulfurization mechanism with ZMC and ZGMC.

There are two routes for sulfur removal from DBT, namely, hydrogenation (HYD) and hydrogenolysis or direct desulfurization (DDS) as shown in FIG. 11. In case of hydrogenation, tetrahydro and hexahydro dibenzothiophene are obtained as intermediate products for DBT. Then, desulfurization occurs to form cyclohexyl benzene and finally bicyclohexyl. While, in the DDS mechanism, no intermediate products are formed as DBT is desulfurized directly to form biphenyl.

Figure 12A:
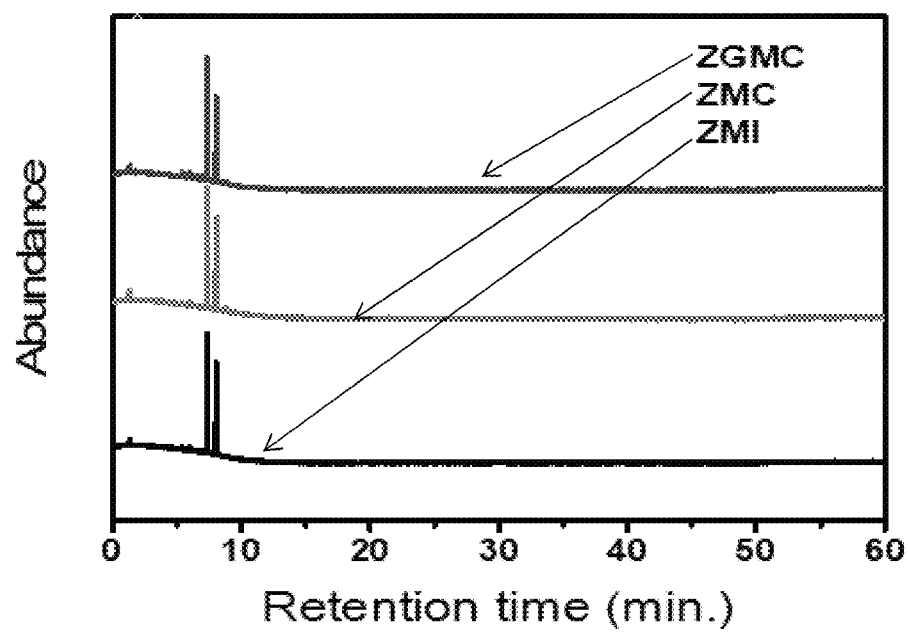
FIGS. 12A-12C illustrate the chromatogram of DBT hydrodesulfurization over ZGMC (12A) GC-MS fragments for biphenyl product (12B) and for bi-cyclohexyl product (12C)
Figure 12B:
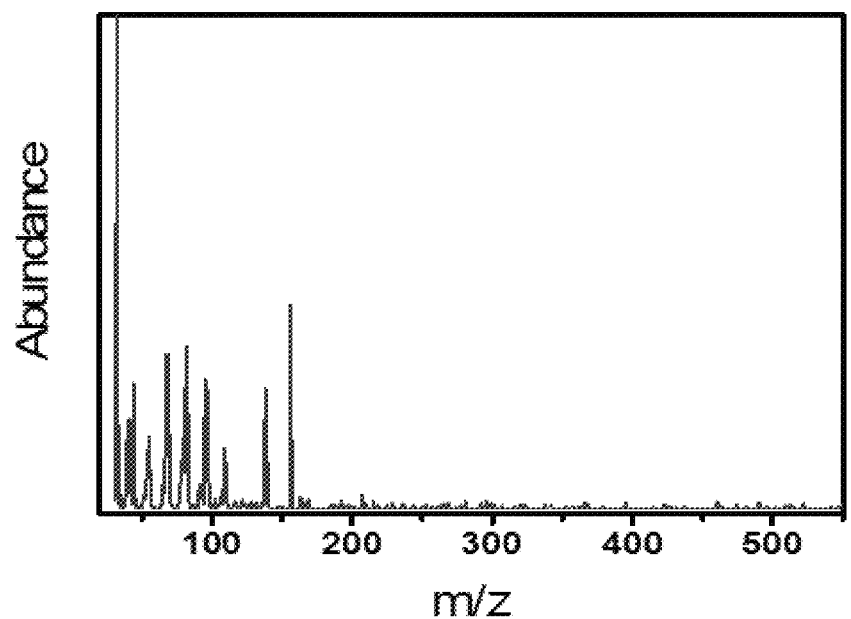
Figure 12C:
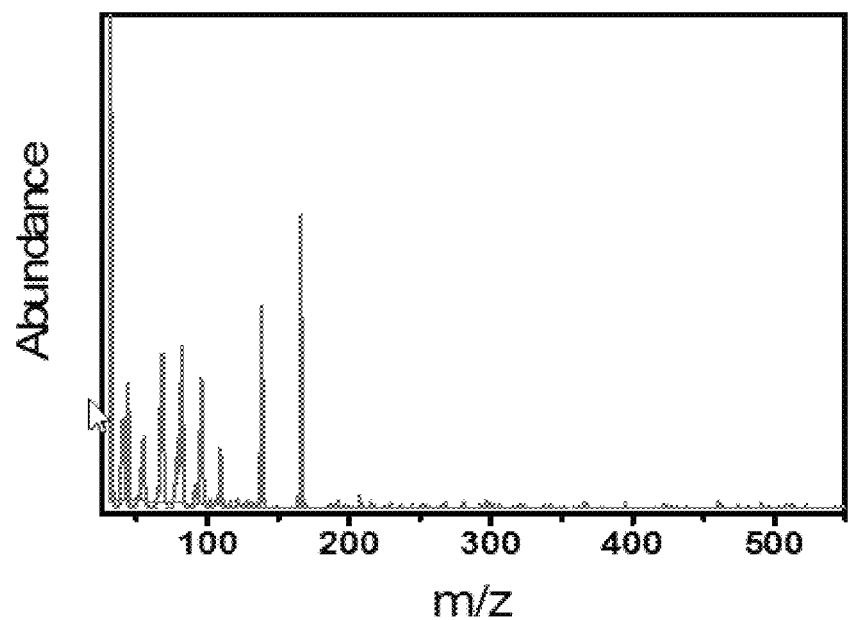

The reaction mechanism of dibenzothiophene hydrodesulfurization over the synthesized catalysts are now described. Product analysis in GC-MS was used to illustrate the proposed desulfurization mechanism. The mechanism is thought to be hydrogenolysis. DBT was desulfurized by C—S bond breaking to obtain biphenyl (BP). The presence of a hydrogen source will lead to the hydrogenation of biphenyl to get cyclohexyl benzene (CHB). In FIG. 12A, the large number of peaks in the GC-MS spectra may be attributed to high number of products that were separated each analysis. The characteristic peak at 154 m/z in FIG. 12B is related to the biphenyl while the peak at 166 m/z in FIG. 12C was attributed to bicyclohexyl. These results confirm the direct desulfurization pathway for dibenzothiophene over the ZGMC catalyst.

Figure 13:
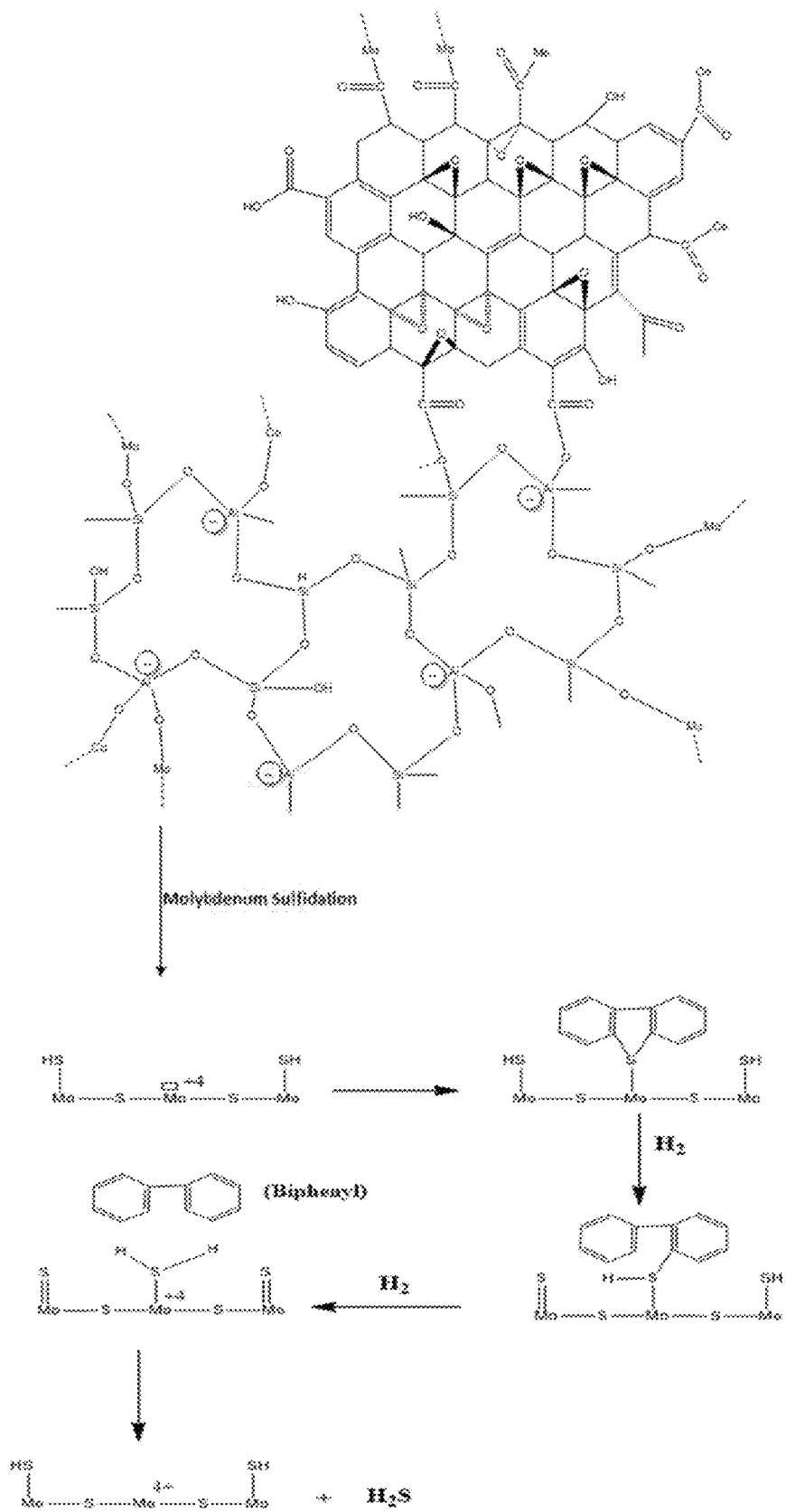
FIG. 13 illustrates the proposed mechanism for the interaction between the composite support and active phases.

FIG. 13 shows a proposed (simplified) structure for the interaction between the graphene material and zeolite, as well as the combination between active phases and the composite support surface. As a final step, C—S bond breaking and releasing of biphenyl from DBT is proposed, and when hydrogen is present during HDS, ultimately the reaction will lead to the formation of bicyclohexyl.

In summary, the higher activity of zeolite-graphene/molybdenum-cobalt (nickel) catalysts compared to zeolite/molybdenum-cobalt (nickel) catalysts for dibenzothiophene removal in hydrodesulfurization reactions was demonstrated. BET data for the synthesized catalysts showed the improvement in the textural properties like surface area and pore size after doping with the graphene material as a co-support with zeolite. SEM images illustrated the enhanced dispersion of the active phases on the support surface in presence of the graphene material. TGA indicted the thermal stability of the prepared catalyst as the % weight loss for ZGMC was 18% while for ZMC was 22%. EDS results confirmed the successful introduction of the nanoparticles active phase on the support surface. The catalyst (ZGMC) evaluation for desulfurization of DBT was found to be superior when compared to the reference samples ZMC and ZMI. The catalyst activity was 98.7% removal of sulfur compared to 94.5% for ZMC. Regarding the mechanism pathway involved during the HDS reaction, it was found to be a direct desulfurization as per the obtained data from GC-MS. Thus, the effective role of graphene material doping within the catalyst to form a composite support was established, and the composite support provided superior activity for sulfur removal.

The invention claimed is:

1. A hydrodesulfurization catalyst, comprising:
a catalyst support comprising a zeolite doped with 0.1 to 0.5 wt. % of a graphene material, based on a total weight of the catalyst support;
5 to 20 wt. % of molybdenum, based on a total weight of the hydrodesulfurization catalyst; and
1 to 6 wt. % of a promoter selected from the group consisting of cobalt and nickel, based on a total weight of the hydrodesulfurization catalyst;
wherein the molybdenum and the promoter are homogeneously disposed on the catalyst support.

2. The hydrodesulfurization catalyst of claim 1, wherein the zeolite is a Y-zeolite.

3. The hydrodesulfurization catalyst of claim 1, wherein the graphene material is present in the catalyst support in an amount of 0.3 to 0.4 wt. %, based on a total weight of the catalyst support.

4. The hydrodesulfurization catalyst of claim 1, wherein the graphene material is graphene oxide.

5. The hydrodesulfurization catalyst of claim 1, wherein molybdenum is present in an amount of 14 to 16 wt. %, and the promoter is present in an amount of 4 to 6 wt. %, each based on a total weight of the hydrodesulfurization catalyst.

6. The hydrodesulfurization catalyst of claim 1, wherein the catalyst support consists of the zeolite doped with the graphene material, and wherein the hydrodesulfurization catalyst consists of the catalyst support, the molybdenum, and the promoter.

7. The hydrodesulfurization catalyst of claim 1, which has a BET surface area of 290 to 350 m$^2$/g.

8. The hydrodesulfurization catalyst of claim 1, which has an average pore diameter of 3 to 3.8 nm.

9. The hydrodesulfurization catalyst of claim 1, which has a total pore volume of 0.25 to 0.30 m$^3$/g.

10. The hydrodesulfurization catalyst of claim 1, which has a hierarchy factor (HF), defined as a ratio of microporous volume to total pore volume ($V_{micro}/V_{total}$) multiplied by a ratio of mesoporous surface area to BET surface area ($S_{meso}/S_{BET}$) of 0.020 to 0.035.

11. A method of producing the hydrodesulfurization catalyst of claim 1, the method comprising:
impregnating the catalyst support by adding an aqueous solution comprising a molybdenum salt and either a cobalt salt or a nickel salt to a suspension of the catalyst support in water to form a catalyst mixture;
filtering the catalyst mixture to obtain a wet catalyst; and
drying and calcining the wet catalyst thereby producing the hydrodesulfurization catalyst.

12. The method of claim 11, wherein the catalyst support is formed by
mixing together the zeolite, the graphene material, water, an alcohol solvent, and a polymeric dispersant to form a support mixture, and
filtering the support mixture to obtain a filtrate and drying the filtrate to form the catalyst support.

13. A method for desulfurizing a hydrocarbon feedstock comprising a sulfur-containing compound, the method comprising:
contacting the hydrocarbon feedstock with the hydrodesulfurization catalyst of claim 1 in the presence of $H_2$ gas to convert at least a portion of the sulfur-containing compound into a mixture of $H_2S$ and a desulfurized product; and
removing the $H_2S$ from the mixture thereby forming a desulfurized hydrocarbon stream.

14. The method of claim 13, wherein the hydrocarbon feedstock is contacted with the hydrodesulfurization catalyst at a temperature of 150 to 500° C. for 0.1-10 hours.

15. The method of claim 13, wherein a pressure of the $H_2$ gas is from 30 to 80 bars.

16. The method of claim 13, wherein the sulfur-containing compound is present in the hydrocarbon feedstock at a concentration of 100 to 7,000 ppm.

17. The method of claim 13, wherein the sulfur-containing compound is at least one selected from the group consisting of a sulfide, a disulfide, a thiophene, a benzothiophene, and a dibenzothiophene.

18. The method of claim 17, wherein the sulfur-containing compound is dibenzothiophene.

19. The method of claim 13, wherein a sulfur content of the desulfurized hydrocarbon stream is less than 10 ppm.

20. The method of claim 13, wherein the hydrocarbon feedstock is contacted with the hydrodesulfurization catalyst by passing the hydrocarbon feedstock through a fixed-bed reactor containing the hydrodesulfurization catalyst.

* * * * *